(12) United States Patent
Qian et al.

(10) Patent No.: US 9,029,133 B2
(45) Date of Patent: May 12, 2015

(54) RECOMBINANT VIRUS COMPRISING AN INTACT TUMOR-THERAPEUTIC ANTIBODY WITH HUMAN CONSTANT REGIONS AND THE USE THEREOF

(76) Inventors: Qijun Qian, Shanghai (CN); Qi Zhang, Shanghai (CN); Qin Yang, Shanghai (CN); Mengchao Wu, Shanghai (CN)

( * ) Notice: Subject to any disclaimer, the term of this patent is extended or adjusted under 35 U.S.C. 154(b) by 1978 days.

(21) Appl. No.: 10/554,902

(22) PCT Filed: Apr. 29, 2004

(86) PCT No.: PCT/CN2004/000430
§ 371 (c)(1),
(2), (4) Date: Nov. 8, 2006

(87) PCT Pub. No.: WO2004/101777
PCT Pub. Date: Nov. 25, 2004

(65) Prior Publication Data
US 2008/0241103 A1 Oct. 2, 2008

(30) Foreign Application Priority Data
Apr. 30, 2003 (CN) .................................. 03 1 16733

(51) Int. Cl.
*C12N 15/861* (2006.01)
*A61K 39/235* (2006.01)
*C07K 16/28* (2006.01)
*C07K 16/32* (2006.01)
*C12N 15/86* (2006.01)
*A61K 39/00* (2006.01)

(52) U.S. Cl.
CPC ................ *C07K 16/32* (2013.01); *A61K 35/13* (2013.01); *A61K 2039/505* (2013.01); *C07K 2317/24* (2013.01); *C12N 15/86* (2013.01); *C12N 2710/10343* (2013.01); *C12N 2750/14143* (2013.01)

(58) Field of Classification Search
None
See application file for complete search history.

(56) References Cited

FOREIGN PATENT DOCUMENTS

CN 1468956 1/2004
WO WO 2004/101777 11/2004

OTHER PUBLICATIONS

Sha et al. (1994) A heavy-chain grafted antibody that recognizes the tumor-associated TAG72 antigen. Cancer Biotherapy 9(4): 341-349.*
Wills et al. (1994) Development and characterization of recombinant adenoviruses encoding human p53 for gene therapy of cancer. Human Gene Therapy 5: 1079-1088.*
Addison et al. (1997) Comparison of the human versus murine *Cytomegalovirus* immediate early gene promoters for transgene expression by adenoviral vectors. J. General Virology 78(7): 1653-1661.*
Xiaozhou, S. et al. "Insulator: a novel genetic regulatory element (a review article)". Bioengineering Progress, vol. 21, No. 6, 2001. pp. 8, 3-7.
Khare, P. et al. "Specifically Targeted Killing of Carcinoembryonic Antigen (CEA)-expressing Cells by a Retroviral Vector Displaying Single-Chain Variable Fragmented Antibody to CEA and Carrying the Gene for lnductible Nitric Oxide Synthase". Cancer Research, vol. 61, Jan. 1, 2001. pp. 370-375.
Graves, S. et al. "Molecular Modeling and Preclinical Evaluation of the Humanized NR-LU-13 Antibody." Clinical Cancer Research, vol. 5, Apr. 1999. pp. 899-908.

* cited by examiner

*Primary Examiner* — Zachariah Lucas
*Assistant Examiner* — Nick Zou
(74) *Attorney, Agent, or Firm* — Ladas & Parry LLP

(57) ABSTRACT

The present invention provides a recombinant virus containing a nucleotide sequence encoding a tumor-therapeutic full-length antibody with human constant regions, and uses thereof. After a nucleotide sequence of a gene encoding a tumor-therapeutic full-length antibody with human constant regions of the light chain and the heavy chain is inserted into the genome of a recombinant virus, the tumor-therapeutic full-length antibody with human constant regions can be efficiently expressed in tumor cells, thereby inhibit the growth and metastasis of tumors.

8 Claims, 2 Drawing Sheets

RECOMBINANT VIRUS COMPRISING AN INTACT TUMOR-THERAPEUTIC ANTIBODY WITH HUMAN CONSTANT REGIONS AND THE USE THEREOF

TECHNICAL FIELD

The present invention relates to a recombinant virus comprising a gene encoding a tumor-therapeutic antibody, in particular to a recombinant virus comprising a gene encoding a tumor-therapeutic full-length antibody with human constant regions. The present invention further relates to the use of said recombinant virus.

BACKGROUND ART

In 1975, Kohler and Milstein established the technique for producing monoclonal antibodies, which provided a new method for treatment of tumors, the targeted therapy of tumors. In the preliminary study of the targeted tumor therapy, great enthusiasm and impractical expectation was held, but the therapeutic effects during the early clinical researches were undesired, mainly because: (1) murine antibodies were exploited in the early clinical researches, which could inducing human antibodies against murine antibodies (HAMA) that could neutralize the therapeutic murine antibodies so that the murine antibodies were quickly cleared off, had a relatively short half-life in human body, and thus their therapeutic effects were uncertain; Moreover, murine antibodies could stimulate allergic responses in human body, thereby may cause toxic negative effects; (2) the affinity and specificity of the antibodies were not high enough, and most antibodies, especially some genetic engineered small molecular antibodies or humanized antibodies had a relatively low affinity and specificity, and thus could not be effectively targeted to tumor cells, so the antitumor effect was not definite in clinic; and (3) success of antibody therapy further depends on the factors of the differences of tumor antigen expression per se and the modulations of antigens. During the recent 5 years, with the development of modem biological technology, two critical techniques with regard to antibody production were solved by scientists, that is: (1) the development of the technology of murine-human chimeric antibodies, humanized antibodies and human antibodies, as well as their production techniques substantially solving the problems associated with the generation of anti-antibodies when murine antibodies were applied to human; in the meantime, because of the use of human Fc fragment (crystallizable fragment, which represents the fragment obtained by digesting immunoglobulin with papain and having a molecular weight of about 50,000) in human-murine chimeric antibodies, humanized antibodies and human antibodies, the half life of the antibodies was extended to several days, even up to 21 days, which was obviously longer than the half life of murine antibodies (shorter than 20 hours); in addition, the modification of human Fc fragment could further improve the effect of killing tumor cells; and (2) with the development of techniques for constructing and screening antibody libraries and for preparing multivalent recombinant antibodies, monoclonal antibodies with high specificity and affinity could be directly obtained, for example, the affinity of an antibody produced by the Selected Lymphocyte Antibody Method (SLAM) is 1000 folds higher than that of an antibody produced by the hybridoma technique. With the development of antibody technologies, the progress of the targeted therapy is finally obtained; some breakthroughs were made during the recent years. The treatment of tumor with antibodies is a promising strategy for the first time.

However, there are still two difficulties in the treatment of solid tumors with antibodies: (1) solid tumor cells are surrounded by dense matrix, so antibodies can hardly penetrate through this barrier to reach tumor cells; obstruction of lymphatic reflux in most solid tumors results in the increase of interstitial pressure and thereby preventing the antibodies in blood from entering the tumor stroma; Even if a small portion of antibodies enters into tumors, they will firstly contact and bind to perivascular tumor cells, and thus cannot reach tumor cells distal to the blood stream; and (2) a great amount of antibody is needed for tumor treatment, which cannot be achieved by the present biological engineering techniques; Moreover, due to the required high quantity and quality of antibodies, the cost of antibody production is very expensive, so that such antibodies are very expensive. Accordingly, the therapeutic effects on large-volume solid tumors with antibodies are undesirable at present. It is suggested in many studies that the antibody therapy for solid tumors should mainly be directed to minor residues of tumor or micrometastasis focus. However, the therapeutic effects of such treatment can only be estimated by a long period study and by a large scale of multicenter clinical trials, which also limits the clinical application of antibodies for treatment of solid tumors.

Gene therapy is a novel method which was developed in recent years for treatment of malignant tumors. The gene transfection methods are classified into two types: viral or non-viral. The viral method usually uses retrovirus, recombinant adenovirus, adeno-associated virus, herpes simplex virus and Vaccinia virus. Retrovirus has relatively high transfection efficiency in vitro, but has relatively low virus titer and relatively low transfection efficiency in vivo; in addition, retrovirus can only infect dividing cells, and has a shortcoming of integrating into cell genomes to cause tumor genesis. Non-viral methods comprise liposome method, gene gun method, etc., but the transgene is expressed for a relatively short period, and the transfection efficiency is lower. Adenovirus and adeno-associated virus are the commonly used viral vectors for gene therapy of tumor at present, and are widely used in many human gene therapy. Adenovirus has advantages of easy production and purification. It can effectively transfect dividing cells and resting cells in vivo and in vitro. Moreover, it will not induce tumor genesis. Adeno-associated virus is capable of transfecting dividing cells and resting cells, and can be expressed permanently. The treatment of tumor with recombinant virus carrying single-chain antibody or Fab antibody has been reported (Alvarez R D, Barnes M N, Gomez-Navarro J, et al., A cancer gene therapy approach utilizing an anti-erbB-2 single-chain antibody-encoding adenovirus (AD21): a phase I trail. Clin. Cancer Res. 2000, 6:3081-7). However, due to the short half-life of the single-chain antibody or Fab antibody in vivo and the lack of antibody-mediated cytotoxicity, their therapeutic effects are undesirable. In contrast, full-length antibodies containing human constant regions, including human-murine chimeric antibodies, humanized antibodies and human antibodies, all have human light-chain constant regions and human heavy-chain constant regions, and thus will have a greatly extended half-life of several days, even up to 21 days. Moreover, said antibodies exhibit an obvious antibody-mediated cytotoxicity.

So far, the use of recombinant virus carrying a gene encoding tumor-therapeutic full-length antibody containing human constant regions is not reported.

DISCLOSURE OF INVENTION

One object of the present invention is to provide a recombinant virus carrying a gene encoding a tumor-therapeutic full-length antibody containing human constant regions.

Another object of the present invention is to provide a recombinant virus carrying a gene encoding a tumor-therapeutic full-length antibody having human constant regions, which can be used to inhibit the growth of tumor cells.

A further object of the present invention is to provide a pharmaceutical composition containing said recombinant virus.

The inventors of the present invention creatively provide a method for tumor treatment by using a recombinant virus carrying a gene encoding a tumor-therapeutic full-length antibody with human constant regions. That is, a recombinant virus carrying a gene encoding a tumor-therapeutic full-length antibody with human constant regions is used to transfect tumor cells or normal cells to express there in a great amount of the tumor-therapeutic full-length antibody containing human constant regions, thereby inhibit the growth and metastasis of tumor. The recombinant virus carrying a gene encoding a tumor-therapeutic full-length antibody having human constant regions of the present invention expresses the tumor-therapeutic full-length antibody containing human constant regions with a high efficiency in tumor tissues. Therefore, the difficulty that full-length antibody can hardly enter solid tumor tissues is overcome.

When a protein is expressed by using a recombinant adenovirus, the expression level of said protein in vivo is generally 0.5-10 μg/ml. However, we surprisingly found out in the present invention that when recombinant adenovirus carrying a gene encoding a tumor-therapeutic full-length antibody with human constant regions was used for treatment, the level of the antibody in blood serum in vivo can be up to 50-150 μg/ml, which is high enough to stimulate therapeutic effects, even obviously higher than the expression level of other genes being carried in a recombinant adenovirus. This may be due to the higher stability of the full-length antibodies with human constant regions in vivo. Such a high concentration in serum enables the full antibody to function effectively in vivo, and thus avoids the trouble some repetitive administration of antibodies. Such an antibody-therapeutic method employing a recombinant adenovirus system carrying a gene encoding a tumor-therapeutic full-length antibody with human constant regions can be further applied in an adeno-associated viral vector system, especially adeno-associated virus type 1 vector system. It can also be used in other vector systems capable of achieving a high-level and long-term expression in vivo.

The recombinant virus carrying a gene encoding a tumor-therapeutic full-length antibody having human constant regions can be produced at a low cost, so that the difficulty of high cost for producing a therapeutic full-length antibody in a large quantity is overcomed. Therefore, the recombinant viruses of the present invention are superior to the antibody therapy in tumor treatment both effectively and economically.

Antibody (Ab) is a glycoprotein capable of specifically binding to a specific antigen. Natural antibody is heterotetrameric glycoprotein with a molecular weight of about 150,000 Daltons, which consists of two identical light chains (L) and two identical heavy chains (H). The light chains link to the heavy chains via covalent disulfide bonds. Each heavy chain consists of one variable region (VH) and several constant regions. Each light chain consists of one variable region (VL) and one constant region. The constant region of the light chain is associated with the first constant region of the heavy chain, and the variable region of the light chain is associated with the variable region of heavy chain.

The relatively conservative regions in the variable regions of an antibody are called as framework regions (FR). The variable regions of natural heavy and light chains separately comprise four framework regions (i.e., FR1, FR2, FR3 and FR4 respectively), and three hypervariable regions are interposed among the four framework regions. The framework regions fold roughly into β-sheet structures that are linked by said three hypervariable regions. The hypervariable regions in each chain are close to each other via the framework regions, and, in combination with the hypervariable regions in another chain, form the antigen-binding site of the antibody.

Complementary determining region (CDR)/the hypervariable region of an antibody represents the amino acid residues of the antibody responsible for binding to its antigen. A hypervariable region comprises amino acid residues from the complementary determining regions (i.e. CDR).

Constant regions do not directly participate in the binding between the antibody and the antigen, yet they are the main sites exhibiting the immunogenicity of the antibody molecule. Therefore, an antibody molecule having human constant regions will show a relatively weak immunogenicity in human body. Human constant regions are critical for the stability of an antibody. The half-life of murine antibodies is less than 20 hours, while the half-life of humanized antibodies or human antibodies is several days, even up to 21 days. In addition, the constant regions of an antibody are also associated with the antibody-mediated cytotoxicity. After an antibody is digested by papain, two identical antigen-binding fragments (Fab fragments, each fragment has one single antigen-binding site) and one residual "Fc" fragment (this name reflects its ability of easy crystallization) are produced. The treatment with pepsin can produce one $F(ab')_2$ fragment, which has two antigen-binding sites and can still crosslink with its antigen.

"Fv" is the smallest antibody fragment, which comprises all antigen-recognizing sites and antigen-binding sites. This region consists of a dimer of one heavy chain variable region and one light chain variable region which are non-covalently linked together closely. In this configuration, the three hypervariable regions in each variable region interact with each other, and define the antigen-binding sites on the surface of the dimer of VH-VL. The six hypervariable regions together determine the antigen-binding specificity of the antibody. However, even a single variable region (or one half of Fv, which merely comprises three variable regions specific for the antigen) may recognize and bind to the antigen, yet with an affinity lower than that of the full binding site.

Fab fragment further comprises the constant region of the light chain and the first constant region of the heavy chain (CH1). Fab' fragment differs from Fab fragment in that the carboxyl terminus of the heavy chain CH1 region contains several additional residues (including one or more cysteines from the hinge region). In the present invention, Fab'-SH represents a Fab' wherein the cysteines in the constant region carry free sulfhydryl groups. $F(ab')_2$ antibody fragments are initially generated as Fab' fragment pair having hinge cysteines therebetween.

Human-murine chimeric antibody is the first studied antibody comprising human constant regions. The binding between an antibody and an antigen completely depends on the variable regions of the antibody, and the constant regions of the antibody are irrelevant to the binding of the antigen. However, the constant regions are the main sites exhibiting its immunogenicity in the antibody molecule. Thus, human-murine chimeric antibody with the constant regions of a murine monoclonal antibody being replaced with human constant regions can eliminate most of the heterology of the antibody in human body, while retain the specificity and affinity of the parent murine monoclonal antibody for binding to its antigen. Since the functional regions of an antibody separately form relatively independent spatial configurations, the substitution of the constant regions is relatively simple. At present, several human-murine chimeric antibodies have been constructed, and four human-murine chimeric antibodies have been approved for sale in U.S.A., namely, ReoPro (a human-murine chimeric antibody against platelet receptor IIbIIIa, which is useful for treatment of coronary heart disease), Rituxan (a human-murine antibody against CD20, which is useful for treatment of lymphoma), Simulect (a human-murine antibody against CD25, which is useful for treatment of graft rejection), and Remicade (a human-murine antibody against TNF-α, which is useful for treatment of inflammatory bowel diseases and rheumatoid arthritis). They have been applied in clinic with good therapeutic effects.

The heterology of a monoclonal antibody cannot be completely eliminated by merely replacing the constant regions of the murine monoclonal antibody with constant regions of a human antibody. The murine sequences in the variable regions may still induce the generation of a human antibody against murine antibody (HAMA) in human body, which may neutralize the therapeutic antibody to be rapidly cleared off. The six hypervariable regions (CDR) in the variable regions of the light and heavy chains form a CDR plane, which directly contacts the antigen and thus determines the specificity of the antibody, while the framework regions (FRs) in the variable regions of the antibody function merely as support of CDR and have a very conservative spatial configuration. Therefore, the murine FRs in the human-murine chimeric antibody can be changed into human FRs to reduce the heterology of the murine monoclonal antibody to a greater extent. Such a monoclonal antibody is called as a humanized antibody. At present, six human-murine chimeric antibodies have been approved for sale in U.S.A, namely, Zanapax (a humanized antibody against CD25, which is useful for treatment of graft rejection), Herceptin (a humanized antibody against Her2, which is useful for treatment of breast cancer), Synagis (a humanized antibody against F protein of respiratory syncytial virus, which is useful for treatment of infections of respiratory syncytial virus), Mylotarg (a humanized antibody against CD33, which is useful for treatment of acute myeloid leukaemia), and CAMPATH (a humanized antibody against CD52, which is useful for treatment of chronic lymphocytic leukaemia). They have been applied in clinic with good therapeutic effects.

Human antibody represents a monoclonal antibody of a complete human origin, and all its variable regions and constant regions are derived from human. Human antibodies can be derived from transgenic mice and antibody libraries, and some of them are in clinical trials.

In the context of the present invention, the term "tumor-therapeutic antibody" means any antibody known in the art to be useful for treating, remitting and/or preventing tumors. The antibody of the present invention comprises human constant regions, and is called full-length antibody in the present invention. It can be a human-murine chimeric antibody, humanized antibody or human antibody. In addition to variable regions, the antibody of the present further further comprises constant regions of a human antibody.

In view of safety, the viral vector used in gene therapy is replication defective, which is deficient in proliferation ability due to the deletion of some essential genes of the virus, usually critical genes responsible for the proliferation and replication of the virus. The critical genes responsible for the proliferation and replication of said virus are transfected into cells to establish a virus packaging cell line. The packaging cell line in combination with the viral vector can produce defective virus that can infect target cells, but cannot replicate or proliferate in target cells because of the deletion of the critical genes responsible for the proliferation and replication of the virus. That is, no subsequent infection will be initiated. Thus, the viral vector deficient in proliferation ability is just a gene carrier, which utilizes the high cell infection efficiency of the virus to bring a desired transgene into target cells.

Insulator

The genome of the recombinant virus of the present invention may comprise at least one nucleotide sequence of insulator in the upstream and downstream of the expression cassette containing a gene encoding a full-length antibody having human constant regions, so that the expression cassette can be expressed repetitively in virus.

It is well known in the art that a mammalian genome consists of noncontinuous chromatin domains. The chromatin domains are some independent control units for gene expression, and will not be affected by the cis elements in adjacent regions. The independency of these domains in terms of function and structure is determined by the boundary elements. Udvardy et al. studied the boundary elements at both termini of hsp70 gene in 87A7 locus of drosophila polytenic chromosome, and found out that the highly nuclease-sensitive regions scs and scs' prevented the genes therebetween in the chromatin domain from being affected by the control elements (positive or negative control) out of said domain. When said regions were inserted between a promoter and an enhancer, the activity of the enhancer on the promoter was effectively inhibited. Since their functions are similar to the insulation effect in electrics, such regions are called insulators. Thereafter, insulators were found in the boundary elements of many chromosomal loci of drosophila (e.g., retrotransposon gypsy, hairy wing repressor, and Fab-7). Insulators are also found in vertebrate chromosomes (e.g., chicken β-globin gene loca, and T-cell receptor gene locus). In addition, it is found in researches that bovine growth hormone transcription stop signal can also function as insulators if positioned flanking a gene expression cassette. Since the β-globin gene locus has been intensively studied, and its chromosomal structure is very conservative, most of the present researches on insulators are based on the chicken β-globin gene locus. Said insulator is a DNA fragment having a length of about 1,200 bp, which is located within the 5' terminal boundary element of the chicken β-globin gene locus. Further researches show that near half of the insulation activity of said fragment is due to a CpG island-like structure (i.e., so-called "core element"), which is located at 5' terminal of said fragment, has a length of about 250 bp and comprises a DNase I hypersensitive site (5'HS4). The content of G+C in said core element is about 70%, wherein the content of CpG dinucleotide sequences is very high (up to 22 sites). Further insulators need to be revealed and further studied to determine whether such a structure commonly exists in all eukaryotic insulators.

Insulator is a boundary element having cis-regulating function. It can block the enhancing or inhibiting effects of adjacent control elements (enhancers or silencers) on the promoter of the gene flanked thereby. Insulators can also protect the gene expression cassette integrated into the genome from the chromosomal position effects. Many models or hypotheses about the mechanism of insulators have been postulated in the art. In general, they can be classified into two main types, i.e., steric models and tracking models. In the steric-model hypothesis, it is believed that two insulators interact sterically with each other to form an ansiform structure which is isolated from the outside, and thereby block the effects of other factors outside the structure, while in the tracking-model hypothesis, it is considered that insulators function as a signal for inhibiting the movement of the enhancer complex toward the promoter along the DNA. At present, there are no sufficient evidences to prove which hypothesis is correct. Nonetheless, it is also possible that insulators may function through multiple mechanisms. Moreover, recent studies have shown that the functions of insulators may be influenced by flanking DNA sequences, indicating that the function mechanism of insulators is very complex. Nevertheless, some beneficial discoveries have been obtained from the researches during the past several years. First, by employing the DNase footprinting method, Gary et al. found a sequence of about 49 bp in the core element of chicken β-globin insulator can also bring about some insulator effect, and they further demonstrated that a known regulator CTCF with zinc fingers can bind closely to said DNA sequence to block the activity of an enhancer. Secondly, the same research group further discovered in a chromosome immunoprecipitation test (ChIP) that the acetylation degree of histidine upstream of the 5'HS4 was very low, and heterochromatin was formed, which was obviously in contrast with the downstream. It was presumed that this might be the critical factor for an insulator to prevent the integrated gene from the chromosomal position effects effectively.

Some breakthroughs were also obtained during the study of the features of insulators. They can be summarized as follows. Firstly, insulators have position specificity, that is, insulators can block the activity of an enhancer only when they are located between the enhancer and the promoter. Secondly, insulators show polarity in the inhibition of the function of an enhancer, that is, they merely inhibit enhancers located at the other side of the boundary where the insulators reside, but show no activity on enhancers located in the same chromosome domain; furthermore, an enhancer that is inhibited by insulators within a domain still exhibits activities on a promoter located in the same domain. Thirdly, insulators exhibit directivity. After studying various combinations, Lieber et al found that maximum insulation function can be achieved when the insulators at both sides are arranged in the same direction as the report gene expression cassette. Finally, the activity of an insulator is copy-number dependent. That is, the activity of two insulator core elements is equivalent to that of the entire 1.2 Kb insulator, and the activity increases with the increase of the copy-number of the insulators.

In the recombinant virus of the present invention, the nucleotide sequence of the insulator comprised therein can be the nucleotide sequence of the insulator from chicken β-globin.

The recombinant virus of the present invention may be a recombinant adenovirus. Human adenoviruses belong to DNA tumor virus family. They can cause benign respiratory tract infections in human beings. Human adenoviruses are divided into 6 types, i.e., types A, B, C, D, E and F, including 1-47 serotypes. Human adenoviruses do not cause cancer in human bodies, but types A and B show some carcinogenicity in rodents, and other human adenoviruses have weak or no carcinogenicity. At present, the adenoviral vectors used in gene therapy are adenoviruses of type C, serotypes 2 and 5, which are free of carcinogenicity. During the infection, viruses maintain a free state in the nuclei of the cells and can effectively transfect dividing and non-dividing cells.

All adenoviral vectors are capable of transfecting dividing cells and non-dividing cells at relatively high transfection efficiency. They do not integrated into human chromosomes and have no carcinogenicity. The disadvantage of adenoviral vectors lies in that the delivered gene cannot be continuously expressed. In general, it is expressed for merely 5-20 days. Such a short-term expression may be caused by the immune response induced by adenoviral proteins.

Adenoviruses can be easily commercially produced in a scale for clinical application. Their virus titer may easily reach $10^{12}$ vp/ml, and the conditions for their storage and transportation are very clear. At present, they are predominantly used in the gene therapy of tumors.

The first generation of adenovirus has an E1 deletion (sometimes an additional E3 deletion). E1 region locates at the left terminus of the genome having a size of 36 kb. It is a protein necessary for the expression of other early and late genes. A deletion of a maximal length of 3150 bp can be made in this region. The expressed protein of E1 region is necessary for the growth of virus. Accordingly, adenovirus with E1 deletion can replicate and proliferate only in some helper cell lines that provide the proteins of E1 region, such as 293, 911 or PER.C6 cell lines, but cannot replicate in most somatic cells. The proteins encoded by E3 region can resist the defense system of the host, but they are unnecessary for the replication of the virus in vitro, so adenovirus with E3 deletion can replicate without helper cell lines in vitro. However, in some cases, it is desirable to maintain or even increase the expression of some proteins in E3 region. For example, the death protein E3-11.6K of adenovirus can promote the release of virus particles from infected cells. The expressed protein of gp19K can reduce the immune response of cytotoxic T-cells in the host against the vector and increase the continuity of the expression of downstream exogenous genes, while the continuous expression of the whole E3 region may not be increased. The maximum capacity for insertion in E3 region is 3.1 kb. Since adenovirus can be packaged in a size of 38 kb without affecting its growth rate and virus titer, a 5.1 kb sequence can be inserted in E1 region, and the insertion capacity will be 8.2 kb when E1/E3 are deleted simultaneously.

The first generation of adenoviral vectors can elicit obvious immune response in vivo, mainly because of the re-synthesis of viral proteins. Thus, the second generation of adenoviral vectors is developed. Many different cell lines have been constructed, which can express E2a DNA binding protein, E2b terminal protein and viral DNA polymerase, all/most of E4 products. The corresponding viral genome deletions allow for the insertion of an expression cassette with a maximum size of 14 kb.

The third generation of adenoviral vector is gutless adenovirus, in which all viral genes are deleted, except for the cis-acting sequences necessary for the replication and packaging of the viral DNA. Theorectically, such a viral vector can carry multi-exogenous genes with a total size of about 37 kb.

The present invention provides a group of recombinant viruses, which are proliferation-deficient recombinant adenoviruses. Preferably, the adenovirus comprises a deletion of E1 region, with or without a further E3 deletion, and said adenoviruses can infect the target cells but can not replicate in them.

In further embodiments, the present invention provides a group of recombinant adenoviruses with E1 deletion and E2 deletion.

The present invention provides a group of recombinant viruses with E1 deletion and E4 deletion.

The present invention provides a group of recombinant viruses, which are gutless recombinant viruses.

The recombinant viruses of the present invention may also be adeno-associated viruses.

Adeno-associated virus (AAV) is a small, nonpathogenic, single-stranded DNA virus, whose replication depends on adenoviruses or herperviruses. Adeno-associated virus per se has two genes, but can encode 7 proteins after different splicing: rep gene encoding the replication and integration functions of the virus, including Rep78, Rep6, Rep52 and Rep40; and cap gene encoding structural components of the virus, including VP1, VP2 and VP3. An inverted terminal repeat sequence (ITRs) is comprised at each end of rep and cap.

A viral vector is constructed by replacing the rep and cap genes with therapeutic genes. Rep proteins and Cap proteins are produced by packaging cells, so the replication of the virus further needs the help of adenovirus proteins. AAV can be site-directedly integrated into chromosome 19 through the rep proteins. However, since the vector cannot produce Reps, it cannot specifically integrated into chromosome 19 afterits the entry into a target cell.

Adeno-associated viruses have high affinity for many cells, so that AAV vectors can be used for many cells. Moreover, the Cap gene of AAV can be easily modified. So many researchers have developed viral vectors for targeting transfection by modifying Cap. In many animal tests, the gene expression of AAV vector continuously exists in long-life cells, such as muscle cells, liver cells, brain cells and the like. The continuous expression is owing to the random integration of the vector, and the presence of some vector DNAs in the form of extrachromosomal DNAs. At present, the ratio of the gene expression originated from the integrated DNAs to that from the extrachromosomal DNAs is still unknown. In the meantime, AAV is very stable, and can be readily stored and transported. The AAV vectors most commonly used in gene therapy are type 2 AAV vectors and type 1 AAV vectors. The latter express a gene of interest at a level several hundred folds, even a thousand folds higher than the former.

Preferably, said adeno-associated viruses are recombinant viruses deficient in proliferation ability.

In the recombinant virus of the present invention, the nucleotide sequence encoding a tumor-therapeutic full-length antibody with human constant regions can be any nucleotide sequence that is known to the person skilled in the art and encodes a full-length antibody having tumor-therapeutic effects and containing human constant regions. Preferably, said nucleotide sequence encoding an tumor-therapeutic full-length antibody with human constant regions is selected from any of the following nucleotide sequences: a nucleotide sequence encoding an anti-neovascularity full-length antibody comprising human constant regions; a nucleotide sequence encoding an antibody against tumor cell growth factor receptor or antibody fragments thereof; a nucleotide sequence encoding a full-length antibody comprising human constant regions against tumor cellular membrane antigen; and a nucleotide sequence encoding an idiotype monoclonal full-length antibody against tumor antigen.

The present invention provides a group of recombinant viruses, wherein said nucleotide sequence encoding a tumor-therapeutic full-length antibody with human constant regions is a nucleotide sequence encoding an anti-neovascularization full-length antibody with human constant regions. The person skilled in the art knows well that all anti-neovascularization full-length antibodies with human constant regions can be used in the present invention. Preferably, said nucleotide sequence encoding an anti-neovascularization full-length antibody with human constant regions is selected from any of the following nucleotide sequences: a nucleotide sequence encoding a full-length antibody with human constant regions against vascular endothelial growth factor; a nucleotide sequence encoding a full-length antibody with human constant regions against vascular endothelial growth factor receptor 2; a nucleotide sequence encoding an anti-integrin $\alpha v \beta 3$ full-length antibody with human constant regions; and a nucleotide sequence encoding a full-length antibody inhibiting vascular endothelial growth and containing human constant regions.

Vascular endothelial growth factor (VEGF) promotes angiogenesis, and plays a key role in oncogenesis and metastasis. Antibodies against vascular endothelial growth factor and fragments thereof can block the binding of the vascular endothelial growth factors to their respective receptors (especially vascular endothelial growth factor receptor 2), inhibit the angiogenesis in tumors, and thereby inhibit the growth and metastasis of tumors. A chimeric antibody against vascular endothelial growth factor (Avastin, also called "Bevacizumab") of Genentech Inc. (US) is in the phase III clinical trial for treatment of advanced solid tumors. The antibody IMC-1C11 of ImClone Systems Inc. (US) against vascular endothelial growth factor receptor 2 (KDR) is in the phase I clinical trial for treatment of tumors. Integrin $\alpha v \beta 3$ participates in the angiogenesis via the signal transmission between intercellular matrix and endothelial cells. Therefore, an antibody against integrin $\alpha v \beta 3$ can inhibit angiogenesis, thereby inhibiting the oncogenesis.

The present invention provides a group of recombinant viruses, wherein the gene encoding a tumor-therapeutic full-length antibody with human constant regions is a nucleotide sequence encoding a full-length antibody with human constant regions against tumor cell growth factor receptor. The person skilled in the art knows well that all full-length antibodies with human constant regions against tumor cell growth factor receptor can be used in the present invention. Preferably, said nucleotide sequence encoding a full-length antibody with human constant regions against tumor cell growth factor receptor is selected from any of the following nucleotide sequences: a nucleotide sequence encoding a full-length antibody with human constant regions against epidermal growth factor receptor 1, and a nucleotide sequence encoding a full-length antibody with human constant regions against epidermal growth factor receptor 2.

Human epidermal growth factor receptors play a critical role in the transformation of various malignant tumor cells. They are overexpressed in many tumor cells. Human epidermal growth factor receptors are also called as ErbB receptors. Four members have been identified at present, which separately are: epidermal growth factor receptor 1 (HER 1, also called as ErbB1 or EGFR), epidermal growth factor receptor 2 (HER2, also called as ErbB2 or Neu), epidermal growth factor receptor 3 (HER3, also called as ErbB3), and epidermal growth factor receptor 4 (HER4, also called as ErbB4). The tumor cell growth can be inhibited by blocking the signaling of epidermal growth factor receptors. The chimeric antibody IMC-C225 against epidermal growth factor receptor 1 (ImClone Systems Inc., US) exhibits obvious therapeutic effects on various advanced tumors, and said antibody is in the phase III and IV clinical trials at present. The human antibody ABX-EGF against epidermal growth factor receptor 1 (Abgenix Inc., US) exhibits obvious therapeutic effects on various advanced tumors, and said antibody is in the phase II clinical trial at present. The humanized antibody Herceptin (also called as Trastuzumab) against epidermal growth factor receptor 2 (Genentech Inc., US) was approved by FDA (US) for clinical application in 1998, which in combination with chemotherapy exhibits obvious therapeutic effects. Another humanized antibody 2C4 epidermal growth factor receptor 2 (Genentech Inc., US) is in the phase I clinical trial.

The present invention provides a group of recombinant virus, wherein the gene encoding a tumor-therapeutic full-length antibody with human constant regions has a nucleotide sequence encoding a full-length antibody containing human constant regions against tumor cellular membrane antigen. In the recombinant virus of the present invention, the nucleotide sequence encoding a full-length antibody with human constant regions against tumor cellular membrane antigen includes, but is not limited to the encoding nucleotide sequences. The person skilled in the art knows well that all full-length antibodies containing human constant regions against tumor cellular member antigen can be used in the present invention. Said nucleotide sequence encoding a full-length antibody containing human constant regions against tumor cellular membrane antigen can be selected from any of the following nucleotide sequences: a nucleotide sequences encoding an anti-CD20 full-length antibody containing human constant regions, a nucleotide sequence encoding an anti-CD52 full-length antibody with human constant regions, and a nucleotide sequence encoding an anti-MUC1 full-length antibody containing human constant regions.

Since CD20 exists in all B lymphocytes, anti-CD20 antibody can kill all B lymphocytes, thereby reduce greatly the generation of antibodies against the adenoviral vector, making it possible for repetitive use of adenoviral vector. In the meantime, B cell lymphoma per se is deficient in antibody production, which may also result in the decrease of antibodies against adenoviral vectors. Thus, anti-CD20 full-length antibodies with human constant regions exhibit obvious therapeutic effects in treatment of B cell lymphoma. The anti-CD20 chimeric antibody Rituxan (also called Rituximab) of Genentech Inc., US is useful for the treatment of B-cell lymphoma, which was approved for clinical application in 1997.

CD52 is highly expressed on surfaces of most normal cells and malignant mature lymphocytes (including T lymphocyte and B lymphocyte), but is not expressed in hemopoietic stem cells. Anti-CD52 antibody can kill all mature lymphocytes, thereby reduce greatly the generation of anti-adenovirus antibodies and T-cell immunological response, making it possible for repetitive use of adenovirus. Thus, tumor-therapeutic adenoviruses carrying a gene encoding an anti-CD52 full-length antibody with human constant regions exhibit obvious therapeutic effects in treating lymphomas. Anti-CD20 humanized antibody Campath was approved for the clinical application for treating chronic lymphocytic leukaemia in 2001.

MUC1 widely exists in most tumors. The anti-MUC1 humanized antibody of Antisoma Inc. (US) is in the clinical trial.

The present invention provides a group of recombinant viruses, wherein the gene encoding a tumor-therapeutic full-length antibody with human constant regions has a nucleotide sequence encoding an idiotypic monoclonal full-length antibody against tumor antigen. The person skilled in the art knows well that all idiotypic monoclonal full-length antibodies against tumor antigen can be used in the present invention. Preferably, said nucleotide sequence encoding an idiotypic monoclonal full-length antibody against tumor antigen is selected from any of the following nucleotides: a nucleotide sequence encoding an anti-17-1A idiotypic monoclonal full-length antibody, a nucleotide sequence encoding an idiotypic monoclonal full-length antibody against carcino-embryonic antigen, a nucleotide sequence encoding an anti-GD3 idiotypic monoclonal full-length antibody, and a nucleotide sequence encoding an anti-MUC1 idiotypic monoclonal full-length antibody.

Anti-idiotypic monoclonal antibody (anti-idiotypic mAb, also represented by Ab2) is also called as anti-idiotype antibody, which mimics the antigens on the surface of tumor cells, and may cause cytotoxic T cell and helper T cell response, thereby treat tumors. 17-1A is highly expressed in tumor cells derived from epithelium. The anti-17-1A idiotypic monoclonal antibody Panorex (Glaxo Wellcome/Centocor Inc.) was approved for treatment of colon cancer in Germany in 1997. The antibody IMC-1C11 against The anti-GD3 idiotypic monoclonal antibody BEC2 (ImClone Systems Inc., US) is in the phase III clinical trial for tumor treatment.

The present invention provides a group of recombinant viruses, wherein the nucleotide sequence encoding a tumor-therapeutic full-length antibody with human constant regions is selected from any of the following nucleotide sequences: a nucleotide sequence encoding IgG and a nucleotide sequence encoding IgM.

The light chain of a vertebrate antibody (immunoglobulin) can be classified into two distinct types: kappa (κ) and lambda (λ), depending on its amino acid sequences in the constant regions.

Depending on the amino acid sequences of the heavy chain constant regions, immunoglobulins can be classified into different types. There are 5 main types of immunoglobulins: IgA, IgD, IgE, IgG and IgM, and some types may be further classified in to several subtypes (isotypes), such as IgG-1, IgG-2, IgG-3, IgG-4, IgA-1 and IgA-2. The constant regions of the heavy chain in different types of immunoglobulins are called as α, β, ε, γ and μ, respectively. The structures and three-dimensional configurations of the subunits in different types of immunoglobulins are well known in the art.

The present invention provides a group of recombinant viruses, wherein the nucleotide sequence encoding a tumor-therapeutic full-length antibody with human constant regions is fused to the nucleotide sequence of a tumor-therapeutic gene to form a fusion gene. Said tumor-therapeutic gene can be any gene which shows a tumor-therapeutic effect, such as one of the following: antiangiogenesis genes, cytokine genes, prodrug convertase genes, and cytotoxic genes.

Said tumor-therapeutic gene can be antiangiogenesis genes. The antiangiogenesis genes can inhibit the neovascularization in tumors, thereby block the nutrient supply for tumor cells, so that tumor cells die of the lack of nutrient, and tumors obviously regress and even completely disappear. In the meantime, the inhibition of neovascularization in tumors will also block the pathway of tumor metastasis. The person skilled in the art knows well that any gene having antiangiogenesis effect can be used in the present invention. The nucleotide sequence of said antiangiogenesis gene can be selected from any of the following: endostatin gene, angiostatin gene, the nucleotide sequence encoding any of Kringle1-4 domain, Kringle1-5 domain, Kringle1-3 domain, Kringle1-3+Kringle5 domains of plasminogen, thrombospondin gene, platelet factor 4 gene, plasminogen activator inhibitor (PAI) gene, and fibronectin gene.

Said tumor-therapeutic gene can also be cytokine genes. Cytokine genes can activate immunologic cells, and promote haematopoiesis, etc. The person skilled in the art knows well that any gene exhibiting cytokine function can be used in the present invention. Said cytokine gene can be one selected from any of the following: interleukin 2, interleukin 12, granulocyte-macrophage colony stimulating factor, tumor necrosis factor, interferon-α, interferon-β, interferon-γ, Light or Flt3 ligand. Said tumor-therapeutic genes can also be prodrug converase genes. Prodrug convertase genes can convert nontoxic drug into toxic drug, thereby enhancing the killing of tumor cells. The person skilled in the art knows well that any prodrug convertase gene can be used in the present invention. The nucleotide sequence of said prodrug convertase gene can be selected from any of the following: recombinant herpes simplex virus thymidine kinase, bacteria β-lactamase, and *E. coli* cytosine deaminase.

The recombinant viruses of the present invention can also comprise a nucleotide sequence of a toxin gene. The person skilled in the art knows well that any toxin gene can be used in the present invention. For example, the nucleotide sequence of said toxin gene can be a sequence encoding a fragment of pseudomonal exotoxin. In the recombinant viruses of the present invention, the nucleotide sequence encoding the tumor-therapeutic full-length antibody with human constant regions is under the control of a promoter. Any promoter exhibiting the activity of a promoter can be used in the present invention. Said promoter can be selected from any of the following promoters: Simian virus 40 (SV40) promoter, Rous Sarcoma virus (RSV) LTR promoter, human cytomegalo virus (HCMV) IE promoter, murine cytomegalo virus (MCMV) IE promoter, and human adenovirus major late promoter (MLP). In the recombinant viruses of the present invention, an intron can be inserted between the transcriptional initiation site of the promoter for controlling the expression of the gene encoding the tumor-therapeutic full-length antibody with human constant regions and the translational start site of said antibody. The insertion of an intron can greatly increase the expression level of the antibody. The person skilled in the art knows well that any intron capable of increasing the expression level of the antibody can be used in the present invention. Said intron can be a hybrid intron, such as one selected from the following introns: the hybrid intron comprising the 5' splicing site of the third leader sequence of adenovirus major later mRNA and the 3' splicing site of immunoglobin, and the hybrid intron comprising the 5' splicing site of the first leader sequence of adenovirus major later mRNA and the 3' splicing site of immunoglobin.

A nucleotide sequence encoding a tumor-therapeutic full-length antibody with human constant regions is inserted in the genome of the recombinant viruses of the present invention. Said nucleotide sequence encoding the tumor-therapeutic full-length antibody with human constant regions can be a nucleotide sequence encoding antiangiogenensis full-length antibody with human constant regions, a nucleotide sequence encoding an antibody against tumor cell growth factor receptor or fragments thereof, or a nucleotide sequence encoding a full-length antibody with human constant regions against tumor cellular membrane antigen. When tumor cells are infected with the recombinant viruses, the tumor cells efficiently express the tumor-therapeutic full-length antibody with human constant regions, thereby inhibit the angiogenesis in tumors, oncogenesis, and growth and metastasis of tumors.

The recombinant viruses of the present invention can also be used to infect normal cells. When normal cells are infected with the recombinant viruses, said normal cells efficiently express tumor-therapeutic full-length antibody with human constant regions, thereby inhibit the angiogenesis in tumors, oncogenesis, and growth and metastasis of tumors.

In one aspect of the present invention, a method for tumor treatment by using the recombinant viruses of the present invention is provided, which comprises the following steps: 1) infecting tumor cells with said recombinant viruses in vivo or in vitro; 2) expressing a tumor-therapeutic full-length antibody comprising human constant regions in tumor cells to inhibit the formation, growth and metastasis of tumors. In the present invention, mammals include, but are not limited to human, monkey, bovine, caprine, swine, dog, cat, etc.

In another aspect of the present invention, a method for tumor treatment in a mammal, especially a human by using the recombinant viruses of the present invention is provided, which comprises administering a chemical anti-neoplastic agent before, when and/or after the tumor cells are infected with the recombinant viruses of the present invention.

In a further aspect of the present invention, a method for tumor treatment by using the recombinant viruses of the present invention is provided, which comprises the following steps: 1) infecting normal cells with said recombinant viruses in vivo or in vitro; 2) expressing tumor-therapeutic full-length antibody with human constant regions in normal cells to inhibit the formation, growth and metastasis of tumors. In the present invention, mammals include, but are not limited to human, monkey, bovine, caprine, swine, dog, cat, etc.

In a further aspect of the present invention, a method for tumor treatment in a mammal, in particular human by using the recombinant viruses of the present invention is provided, which comprises administration of chemical anti-neoplastic agent before, when and/or after the normal cells are infected with the recombinant viruses of the present invention.

In order to further improve the therapeutic effect, the recombinant viruses of the present invention, which are capable of efficiently expressing tumor-therapeutic full-length antibody with human constant regions, can be used in combination with conventional chemotherapeutic drugs (such as cisplatin, 5-fluorouracil, mitomycin C, etc.), biotoxins (such as ophiotoxin), tumor-therapeutic monoclonal full-length antibodies with human constant regions to treat tumors with better effect. In a further aspect of the present invention, the recombinant viruses of the present invention are used in combination with X-ray to result in more effective antitumor effects.

The present invention provides a group of recombinant viruses, which can replicate and proliferate in tumor cells, thereby specifically inhibit the growth of tumor cells. In an another further aspect of the present invention, use of the recombinant viruses of the present invention for inhibiting tumor growth is provided.

The recombinant viruses can be delivered to target cells via a variety of routes, including, but not limited to liposomes, conventional transfection methods known in the art (such as calcium phosphate precipitation, or electroporation), direct injection, and intravenous perfusion. The selection of the delivery method depends on specific recombinant virus (including its configuration), and types and locations of the target cells (i.e., cells in vivo or in vitro).

If a packaged recombinant virus is to be used, it can be administered at a dosage of about $10^4$-$10^{14}$ in a suitable physiologically acceptable carrier. The multiplicity of infection usually ranges from about 0.001 to 100. If it is administered in the form of a polynucleotide (i.e., without being packaged into a recombinant virus), its dosage may be from about 0.01 μg to about 1000 μg. The specific amount for administration can be determined on the basis of the common knowledge in the field about the recombinant viruses (such as the published documents), or empirically. The recombinant viruses can be administered in a single or multiple dosage(s), which depends on the intended use and the capability of immune response of the host. The recombinant viruses can also be administered by multiple injections simultaneously. If the generation of immune response is undesirable, various immunosuppressive agents can be used to reduce immune response, so that repetitive administration can be carried out without inducing strong immune response.

The present invention further provides a composition, such as a pharmaceutical composition, which comprises the recombinant viruses of the present invention. Said composition can be administered in vivo. Preferably, said composition further comprises a pharmaceutically acceptable excipient. The composition comprising an effective amount of recombinant viruses of the present invention in a pharmaceutically acceptable excipient can be systemically administered to a subject in the form of unit dosage, a sterile parenteral solution or suspension, a sterile nonparenteral solution or oral solution or suspension, an oil-in-water or water-in-oil emulsion, etc. The formulations for delivery of nonparenteral and parenteral drugs are well known in the art (see also, Remington's Pharmaceutical Sciences, 18$^{th}$ Edition, Mack Publishing, 1990). The pharmaceutical composition further comprises the lyophilized form and/or reconstituted form of the recombinant viruses of the present invention (including those packaged into recombinant viruses).

The present invention further provides a method for treatment of diseases, comprising administering the recombinant viruses of the present invention at in effective amount to an individual. The treatment method of using recombinant viruses can be applied to a patient with a tumor (such as hepatoma), or to a population at a high risk of tumorgenesis, such as individuals with a family history of such a disease and/or individuals who had been subjected to excision or other treatment (such as chemotherapy) of a disease. The administration of the recombinant viruses of the present invention can be determined particularly by several assessable clinical parameters, such as serological indexes and histological examination of tissue biopsy. Generally, the pharmaceutical compositions comprising the recombinant viruses are administered, as discussed above. The amount of recombinant viruses to be administered depends on various factors, such as the specific type of the recombinant virus, the route of administration, the health status of the individual, the development of the disease, and the specific tumor-therapeutic gene being used.

If a packaged recombinant virus is to be administered, its dosage may be about $10^4$ to about $10^{14}$, preferably about $10^4$ to about $10^{12}$, more preferably about $10^4$ to $10^{10}$. If a polynucleotide is administered, its dosage may be about 0.01 µg to about 100 µg, preferably 0.1 µg to about 500 µg, more preferably about 0.5 µg to about 200 µg. It is possible to administer more than one recombinant virus simultaneously or sequentially. It is usually administered periodically while monitoring any response. It can be administered intratumorally, intravenously or intraperitoneally.

As compared with other tumor therapeutic methods, the present invention has the following advantages.

The present invention provides a group of recombinant viruses for treating tumors.

The animal tests demonstrated that said recombinant viruses can be used for treatment of tumors.

The present invention can be used for killing tumor cells in vivo and in vitro, without substantially affecting normal cells. The recombinant viruses can efficiently express tumor-therapeutic full-length antibody with human constant regions in tumor cells in vivo and in vitro. They can be administered in combination with chemical antitumoral agents to kill tumor cells more effectively, thereby treat tumors efficiently, with little or no toxicity.

Human adenoviruses can be classified into 6 different subgenera, namely A, B, C, D, E and F, which are different in terms of host cell tropism, oncogenicity, and pathogenicity history. The present invention is illustrated with adenovirus subgenus C type 5 (Ad5). All construction methods in the present invention can be easily carried out by the person skilled in the art.

EXAMPLES

Example 1

Figure 1:
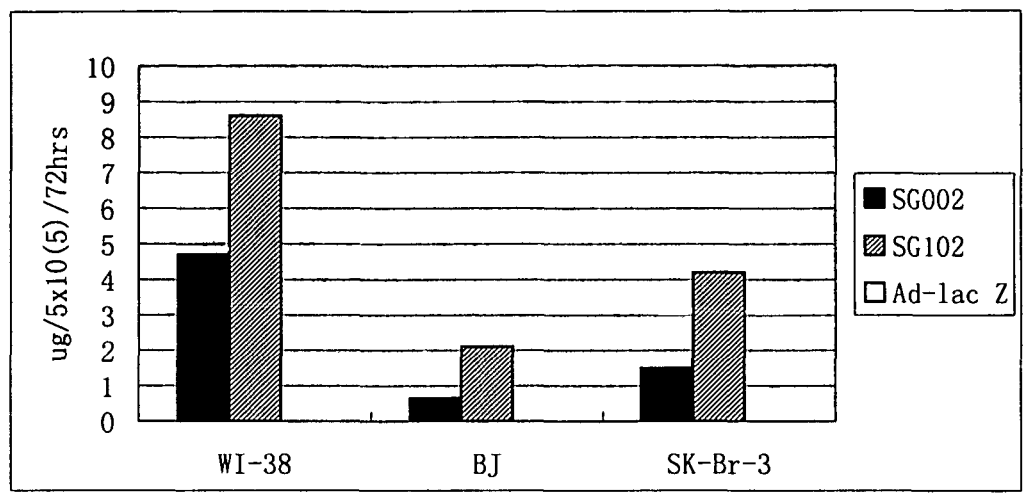
FIG. 1: the expression levels of the humanized antibodies in the supernatants of WI-38, BJ and SK-Br-3 cells that are infected by the recombinant viruses SG002, SG102 and the control adenovirus Ad5-Lac Z in vitro.

Construction of the Expression Vectors Separately Carrying a Gene (SG-EGFR) Encoding Human Antibody Against Human Epidermal Growth Factor Receptor 1 (EGFR), or a Gene Encoding Humanized Antibody (SG-HER) Against Human Epidermal Growth Factor Receptor 2 (Her2), or a Gene Encoding Human-Murine Chimeric Antibody Against Human CD20 pShuttle-CMV was commercially available from Qbiogene (US), which comprised human cytomegalo virus promoter (CMV IE) and SV40 poly A signal. The human cytomegalovirus virus promoter (CMV IE) and SV40 poly A were cloned by PCR, and site-directed double PCR was employed to add Bgl II cleavage sites to the upstream and the downstream, and to insert multiple cloning sites (MCS) between the human cytomegalo virus promoter (CMV IE) and the SV40 poly A signal, which contained the restriction sites for the following enzymes: EcoR I, Sal I, Hind III, Xho I and BamH I (sell also PCR Protols Current Methods and Applications, edited by White B A, Humana Press Inc., 1993, "Document 1"). A fragment of 621 bp was produced by PCR using the following primer 1 and primer 2, with pShuttle-CMV as template.

```
Primer 1:
                                        (SEQ ID NO: 1)
GGG GTA CCT AGA TCT TAG TAA TCA ATT ACG GGG TCA Primer 2:
                                        (SEQ ID NO: 2)
```

```
GAG AAG CTT GTC GAC GAA TTC CTA GCG GAT CTG ACG

GTT CAC
```

A fragment of 293 bp was produced by PCR using the following primer 3 and primer 4, with pShuttle-CMV as template.

```
Primer 3:
                                        (SEQ ID NO: 3)
GAA TTC GTC GAC AAG CTT CTC GAG GGA TCC ATC TAG

ATA ACT GAT CAT A

Primer 4:
                                        (SEQ ID NO: 4)
ATA GTT TAG CGG CCG CTA AGA TCT AAG ATA CAT TGA

TGA GTT TG
```

PCR was conducted to produce a fragment of 893 bp by using primer 1 and primer 4, with the above fragments as templates. After digested by KpnI and NotI, the fragment was inserted into pBluescript. The resulting plasmids were sequenced, and one clone with the correct sequence was named pClone 1. After digested by Bgl II, a fragment of 861 bp was obtained.

The polycistron (IRES) of encephalomyocarditis virus (EMCV) was from pIRES-EYFP, which was commercially available from Clontech Inc. (US). A fragment of 624 bp was produced by PCR using the following primer 5 and primer with 6, with said plasmid as template.

```
Primer 5:
                                        (SEQ ID NO: 5)
CCG GAA TTC ATC GAT TCT GTC GAC CTG CAG GAA TTG

CCC CTC TCC CTC

Primer 6:
                                        (SEQ ID NO: 6)
TGC TCT AGA CCC GGG CTC GAG GGA TCC TTA ATC ATC

GTG TTT TTC AAA G
```

The resulting fragment was double-digested by EcoRI+XbaI and subcloned into the plasmid pUC19. The resulting plasmid was sequenced and named as pUC19-IRES.

The resulting fragment was digested by EcoRI+XbaI and inserted into pClone 1 between the restriction sites of EcoRI and XbaI. The resulting plasmid was called pClone 2.

The plasmid pClone 2 was a dual gene expression vector containing the polycistron (IRES) of encephalomyocarditis virus (EMCV), the promoter being human cytomegalovirus promoter (CMV IE). The plasmid has two multiple clone sites (MCS): the first MCS contains the restriction sites for the following enzymes in sequence: EcoR I, Cla I, Sal I and Pst I, and the second MCS contains the restriction sites for the following enzymes in sequence: BamH I, Xho I, Xma I and Xba I.

The whole sequences of the genes encoding the human antibody SG-EGFR against human epidermal growth factor receptor 1 (EGFR) were synthesized in Shanghai Justbest Gene Technology Inc., with the variable regions of the light chain and the heavy chain identical to the variable regions in the light chain gene and the heavy gene encoding the human antibody ABX-EGF of Abgenix Company (US) against epidermal growth factor receptor 1. The pUC19 plasmid containing the heavy chain gene of SG-EGFR with a BamH I restriction site upstream and a Xba I restriction site downstream of the heavy chain was called pUC-SG-EGFRH. The pUC19 plasmid containing the light chain gene of SG-EGFR with an EcoR I restriction site upstream and a Sal I restriction site downstream of the light chain was called pUC-SG-EGFRL.

The nucleotide sequence of the heavy chain gene of SG-EGFR was:

```
5'CGCGGATCCACCATGGAGTTTTGGCTGAGCTGGGTTTTCCTTGTTGCTATTTTAAAAGGTGTCCAGTG
     BamHI         heavy chain signal peptide
   TGTCTCTGGTGGCTCCGTCAGCAGTGGTGATTACTACTGGACCTGGATTCGGCAGTCCCCAGGGAAGGG
```

Variable region starts

```
ACTGGAGTGGATTGGACACATCTATTACAGTGGGAACACCAATTATAACC

CCTCCCTCAAGAGTCGACTCACCATATCAATTGACACGTCCAAGACTCAG

TTCTCCCTGAAGCTGAGTTCTGTGACCGCTGCGGACACGGCCATTTATTA

CTGTGTGCGAGATCGAGTGACTGGTGCTTTTGATATCTGGGGCCAAGGGA

CAATGGTCACCGTCTCTTCAGCCTCCACCAAGGGCCCATCGGTCTTCCCC

CTGGCACCCTCCTCCAAGAGCACCTC
```

Variable region ends, constant regions start

Constant regions end

```
                                        (SEQ ID NO: 7)
TGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACC

TTCCCGGCTGTCCTACAGTCCTCAGGACTCTACTCCCTCAGCAGCGTGGT

GACCGTGCCCTCCAGCAGCTTGGGCACCCAGACCTACATCTGCAACGTGA

ATCACAAGCCCAGCAACACCAAGGTGGACAAGAAAGTTGAGCCCAAATCT

TGTGACAAAACTCACACATGCCCACCGTGCCCAGCACCTGAACTCCTGGG

GGGACCGTCAGTCTTCCTCTTCCCCCCAAAACCCAAGGACACCCTCATGA

TCTCCCGGACCCCTGAGGTCACATGCGTGGTGGTGGACGTGAGCCACGAA

GACCCTGAGGTCAAGTTCAACTGGTACGTGGACGGCGTGGAGGTGCATAA

TGCCAAGACAAAGCCGCGGGAGGAGCAGTACAACAGCACGTACCGTGTGG

TCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCAT

CTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTC
```

-continued
AAAGGCTTCTATCCCAGCGACATCGCCGTGGAGTGGGAGAGCAATGGGCA

GCCGGAGAACAACTACAAGACCACGCCTCCCGTGCTGGACTCCGACGGCT

CCTTCTTCCTCTACAGCAAGCTCACCGTGGACAAGAGCAGGTGGCAGCAG

GGGAACGTCTTCTCATGCTCCGTGATGCATGAGGCTCTGCACAACCACTA

CACGCAGAAGAGCCTCTCCCTGTCTCCGGGTAA<u>A</u>TAGTAA<u>TCTAGA</u>AAGC

TTGGG 3'.                                                            Xba I

The nucleotide sequence of the light chain gene of SG-EGFR was:

5'CCG<u>GAATTC</u>ACC|ATGGAAGCCCCAGCTCAGCTTCTCTTCCTCCTGCTACTCTGGCTCCCAGATACCAC|
    EcoR I                      light chain signal peptide
|CGGA|ACCATCACTTGCCAGGCGAGTCAGGACATCAGCAACTATTTAAATTGGTATCAGCAGAAACCAGG Variable region starts

GAAAGCCCCTAAACTCCTGATCTACGATGCATCCAATTTGGAAACAGGGG

TCCCATCAAGGTTCAGTGGAAGTGGATCTGGGACAGATTTTACTTTCACC

ATCAGCAGCCTGCAGCCTGAAGATATTGCAACATATTTCTGTCAACACTT pUC-SG-EGFRL was digested by EcoR I+Sal I, and was directly inserted into pClone2-SG-EGFRH between the EcoR I and the Sal I sites to produce the resulting plasmid pClone2-SG-EGFR.

The full-length genes encoding the humanized antibody SG-HER against human epidermal growth factor receptor 2 (Her2) were synthesized by Shanghai Justbest Gene Technology Inc., the variable regions of the light chain gene and the heavy gene were identical to the variable regions of the light chain gene and the heavy gene of the humanized antibody Herceptin (Genentech Company, US) against epidermal growth factor receptor 2 (see also Carter et al., U.S. Pat. No. 5,821,337) respectively. The pUC19 plasmid containing the heavy chain gene of SG-HER with an BamH I restriction site upstream and an Xho I restriction site downstream of the gene was called pUC-SG-HERH. The pUC19 plasmid containing the light chain gene of SG-HER with an EcoR I restriction site upstream and a Sal I restriction site downstream of the gene to produce was called pUC-SG-HERL.

The nucleotide sequence of the heavy chain gene of SG-HER was:

5'<u>GGATCC</u>ACC|ATGAGCACTGAAAGCATGATCCGGGACGTGGAGCTGGCCGAGGAGGCGCT
   BamH I            TNF signal peptide
|CCCCAAGAAGACAGGGGGGCCCCAGGGCTCCAGGCGGTGCTTGTTCCTCAGCCTCTTCTCC|
|TTCCTGATCGTGGCAGGCGCCACCACGCTCTTCTGCCTGCTGCACTTTGGAGTGATCGGCCC|
|CCAGAGGGAAGAGTTCCCCAGGGACCTCTCTCTAATCAGCCCTCTGGCCCAGGCA|GAGGTT -continued
TGATCATCTCCCGCTCGCTTTCGGCGGAGGGACCAAGGTGGAGATCAA<u>A</u>A

CTGTGGC

Variable region ends, and constant regions start

Constant regions end
                                    (SEQ ID NO: 8)
TGCACCATCTGTCTTCATCTTCCCGCCATCTGATGAGCAGTTGAAATCTG

GAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGA

GAGTGTCACAGAGCAGGACAGCAAGGACAGCACCTACAGCCTCAGCAGCA

CCCTGACGCTGAGCAAAGCAGACTACGAGAAACACAAAGTCTACGCCTGC

GAAGTCACCCATCAGGGCCTGAGCTCGCCCGTCACAAAGAGCTTCAACAG

GGGAGAGTG<u>T</u>GATAA<u>GTCGAC</u>3'.
               Sal I pUC-SG-EGFRH was digested by BamH I+Xba I, and directly inserted into pClone2 vector between the BamH I and the Xba I sites to produce plasmid pClone2-SG-EGFRH.

Variable region starts

CAGCTGGTGGAGTCTGGCGGTGGCCTGGTGCAGCCAGGGGGCTCACTCCG

TTTGTCCTGTGCAGCTTCTGGCTTCAACATTAAAGACACCTATATACACT

GGGTGCGTCAGGCCCCGGGTAAGGGCCTGGAATGGGTTGCAAGGATTTAT

CCTACGAATGGTTATACTAGATATGCCGATAGCGTCAAGGGCCGTTTCAC

TATAAGCGCAGACACATCCAAAAACACAGCCTACCTGCAGATGAACAGCC

TGCGTGCTGAGGACACTGCCGTCTATTATTGTTCTAGATGGGGAGGGGAC

GGCTTCTATGCTATGGACTACTGGGGTCAAGGAACCCTGGTCACCGTCTC

CTC<u>G</u>GCCTCCACCAAGGGCC

Variable region ends, and constant regions start

Constant regions end
                                    (SEQ ID NO: 9)
CATCGGTCTTCCCCCTGGCACCCTCCTCCAAGAGCACCTCTGGGGGCACA

GCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTG

-continued

```
TCCTACAGTCCTCAGGACTCTACTCCCTCAGCAGCGTGGTGACCGTGCCC
TCCAGCAGCTTGGGCACCCAGACCTACATCTGCAACGTGAATCACAAGCC
CAGCAACACCAAGGTGGACAAGAAAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCAGTACACGCAGAAG
AGCCTCTCCCTGTCTCCGGGTAAATAGTAACTCGAG 3'.
                              Xho I
```

The nucleotide sequence of the light chain gene of SG-HER was:

```
5'CCGGAATTCACC ATGGAAGCCCCAGCTCAGCTTCTCTTCCTCCTGCTACTCTGGCTCCCAG
    EcoR I         light chain signal peptide
ATACCACCGGA GATATCCAGATGACCCAGTCCCCGAGCTCCCTGTCCGCCTCTGTGGGCGAT
```

Variable region starts

```
AGGGTCACCATCACCTGCCGTGCCAGTCAGGATGTGAATACTGCTGTAGC
CTGGTATCAACAGAAACCAGGAAAAGCTCCGAAACTACTGATTTACTCGG
CATCCTTCCTCTACTCTGGAGTCCCTTCTCGCTTCTCTGGATCCAGATCT
GGGACGGATTTCACTCTGACCATCAGCAGTCTGCAGCCGGAAGACTTCGC
AACTTATTACTGTCAGCAACATTATACTACTCCTCCCACGTTCGGACAGG
```

-continued

```
GTACCAAGGTGGAGATCAAAACTGTGGCTGCACCATCTGTCTTCATCTTC
CCGCCATCTG
```

Variable region ends, and constant regions start

Constant regions end
(SEQ ID NO: 10)

```
ATGAGCAGTTGAAATCTGGAACTGCCTCTGTTGTGTGCCTGCTGAATAAC
TTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCA
CCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGT
CACAAAGAGCTTCAACAGGGGAGAGTGTTGATAAGTCGAC 3'.
                                   Sal I
``` pUC-SG-HERH was digested by BamH I+Xho I, and was directly inserted into the plasmid pClone2 between the BamH I and the Xho I sites to produce pClone2-SG-HERH. The plasmid pUC-SG-HERL was digested by EcoR I+Sal I, and directly inserted into pClone2-SG-HERH vector between the EcoR I and the Sal I sites to produce pClone2-SG-HER.

The full-length gene of the human-murine chimeric antibody SG-CD20 against CD20 was synthesized by Shanghai Justbest Gene Technology Company Limited. The variable regions of the light chain chain and the heavy chain were identical to that of the light chain gene and the heavy chain gene of the human-murine chimeric antibody IDEC-C2B8 against CD20 (Rituximab) (IDEC Company, US) (see also Anderson et al., U.S. Pat. No. 6,399,061) respectively. The pUC19 plasmid containing the heavy chain gene of SG-CD20 with an upstream BamH I restriction site and a downstream Xba I restriction site was called pUC-SG-CD20H. pUC19 plasmid containing the light chain gene of SG-CD20 with an upstream EcoR I restriction site and a downstream Sal I restriction site was called pUC-SG-CD20L.

The nucleotide sequence of the heavy chain gene of SG-CD20 was:

```
5'CGCGGATCCACC ATGGAGTTTTGGCTGAGCTGGGTTTTCCTTGTTGCTATTTTAAAAGGTGTCCAGTG
    BamH I         heavy chain signal peptide
T CAGGTACAACTGCAGCAGCCTGGGGCTGAGCTGGTGAAGCCTGGGGCCTCAGTGAAGATGTCCTGCAA
```

Variable region starts

```
GGCTTCTGGCTACACATTTACCAGTTACAATATGCACTGGGTAAAACAGA
CACCTGGTCGGGGCCTGGAATGGATTGGAGCTATTTATCCCGGAAATGGT
```

-continued
```
GATACTTCCTACAATCAGAAGTTCAAAGGCAAGGCCACATTGACTGCAGA

CAAATCCTCCAGCACAGCCTACATGCAGCTCAGCAGCCTGACATCTGAGG

ACTCTGCGGTCTATTACTGTGCAAGATCGACTTACTACGGCGGTGACTGG

TACTTCAATGTCTGGGGCGCAGGGACCACGGTCACCGTCTCTGCAGCCTC

CACCAAGGGCCCATCGGTCTTCCCCCTGGCACCCTCCTCCAAGAG
```

Variable region ends, and constant regions start

```
Constant regions end
                                        (SEQ ID NO: 11)
CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGATGAGCTGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAATAGTAA

TCTAGA 3'.
 Xba I
```

The nucleotide sequence of the light chain gene of SG-CD20 was:

```
5'CCGGAATTCACC ATGGAAGCCCCAGCTCAGCTTCTCTTCCTCCTGCTACTCTGGCTCCCAGATACCAC
   EcoR I           kappa light chain signal peptide
CGGA CAAATTGTTCTCTCCCAGTCTCCAGCAATCCTGTCTGCATCTCCAGGGGAGAAGGTCACAATGAC
```

Variable region starts

```
TTGCAGGGCCAGCTCAAGTGTAAGTTACATCCACTGGTTCCAGCAGAAGC

CAGGATCCTCCCCCAAACCCTGGATTTATGCCACATCCAACCTGGCTTCT

GGAGTCCCTGTTCGCTTCAGTGGCAGTGGGTCTGGGACTTCTTACTCTCT

CACCATCAGCAGAGTGGAGGCTGAAGATGCTGCCACTTATTACTGCAGC
```

```
AGTGGACTAGTAACCCACCCACGTTCGGAGGGGGGACCAAGCTGGAAATC

AAACGTACTGTGGCTGCACCATCTGT
```

Variable region ends, and constant regions start

```
Constant regions end
                                        (SEQ ID NO: 12)
CTTCATCTTCCCGCCATCTGATGAGCAGTTGAAATCTGGAACTGCCTCTG

TTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGA

GCAGGACAGCAAGGACAGCACCTACAGCCTCAGCAGCACCCTGACGCTGA

GCAAAGCAGACTACGAGAAACACAAAGTCTACGCCTGCGAAGTCACCCAT

CAGGGCCTGAGCTCGCCCGTCACAAAGAGCTTCAACAGGGGAGAGTGTTG

ATAAGTCGAC 3'.
    Sal I
``` pUC-SG-CD20H was digested by BamH I+Xba I, and the obtained fragment was directly inserted into pClone2 between the BamH I and the Xba I sites to generate a plasmid named pClone2-SG-CD20H. pUC-SG-CD20L was digested by EcoR I+Sal I, and was directly inserted into pClone2-SG-CD20H between the EcoR I and the Sal I sites to generate a plasmid named pClone2-SG-CD20.

Example 2

Recombination of Proliferation-Deficient Adenoviruses Respectively Carrying a Gene Encoding a Human Antibody SG-EGFR Against Human Epidermal Growth Factor Receptor 1 (EGFR), a Gene Encoding a Humanized Antibody SG-HER Against Human Epidermal Growth Factor Receptor 2 (her2), and a Gene Encoding a Human-Murine Chimeric Antibody SG-CD20 Against Human CD20

Adenoviral vectors pDC311, pDC315, pBHGlox(delta) E1Cre and pBHGlox(delta)E1,3Cre were commercially available from Microbix Biosystem Inc. (Toronto, Canada).

The plasmid pCone2-SG-EGFR was digested by EcoR I+Xba I, and was directly inserted into the pDC315 between the EcoR I and the Nhe I sites to produce a plasmid named pDC315-SG-EGFR. The plasmid pClone2-SG-HER was digested by EcoR I+Xho I, and was directly inserted into the pDC315 vector between the EcoR I and the Sal I restriction sites. The resulting plasmid was called pDC315-SG-HER. The plasmid pClone2-SG-CD20 was digested by EcoR I+Xba I, and was directly inserted into pDC315 between the EcoR I and the Nhe I sites to produce the resulting plasmid pDC315-SG-CD20.

In order to further increase the expression level of the antibodies, an intron was inserted between the transcriptional initiation site of the promoter and the translational start site of the antibody, which intron is a hybrid intron containing the 5' splicing site of the third leader sequence of adenovirus major later mRNA and the 3' splicing site of immunoglobin. The full nucleotide sequence of said hybrid intron was synthesized by Shanghai Justbest Gene Technology Company Limited, with a Spe I restriction site being introduced upstream of the intron, and an EcoR I restriction site being introduced downstream of the intron. The synthesized intron was inserted into pUC19 to produce a plasmid named pUC-Intron.

The nucleotide sequence of said hybrid intron was:

(SEQ ID NO: 13)
ACTAGTTAACCAGTCACAGTCGCAAGGTAGGCTGAGCACCGTGGCGGGCG

GCAGCGGGTGGCGGTCGGGGTTGTTTCTGGCGGAGGTGCTGCTGATGATG

TAATTAAAGTAGGCGGTCTTGAGACGGCGGATGGTCGAGGTGAGGTGTGG

CAGGCTTGAGATCGATCTGGCCATACACTTGAGTGACAATGACATCCACT

TTGCCTTTCTCTCCACAGGTGTCCACTCCCAGGTCCAACCGAATTC

The following two DNA oligonucleotides were synthesized to form a linker:

Primer 7:
(SEQ ID NO: 17)
AAT TAC TAG TCA GGA ATT CAA GCT TAG ATC TG

Primer 8:
(SEQ ID NO: 18)
CTA GCA GAT CTA AGC TTG AAT TCC TGA CTA GT

These two DNA oligonucleotides were mixed together at an amount of 0.1 µg, denatured at 100° C. for 5 minutes, and then annealed by slow cooling. The resulting linker was phosphorylated with T4 bacteriophage polynucleotide kinase after annealing. The phosphorylated linker was inserted into pDC315 vector between the EcoR I and the Nhe I sites to produce a plasmid named pDC315-Linker. A multiple cloning site containing Spe I, EcoR I, Hind III, Bgl II, Nhe I, BamH I, Sal I and Acc I restriction sites was introduced into pDC315-Linker.

The plasmid pUC-Intron was digested by Spe I+EcoR I, and the obtained fragment was inserted into pDC315-Linker between the Spe I and the EcoR I sites to produce the plasmid pYQ10. The plasmid contains a multiple cloning site including the following restriction sites: EcoR I, Hind III, Bgl II, Nhe I, BamH I, Sal I and Acc I. The plasmid pClone2-SG-HER was digested by EcoR I+Xho I, and directly inserted into pYQ10 between the EcoR I and the Sal I sites to produce a plasmid named pYQ10-SG-HER.

The expression vector pSGEI containing chicken globin insulator was constructed as follows: pUC19 (commercially available from ATCC Company US) was digested by EcoR I and Hind III, and the following two DNA oligonucleotides were synthesized to form a linker:

Primer 9:    AATTGACCGGTAGCTA    (SEQ ID NO: 14)

Primer 10:   GCTTAGCTACCGGTC     (SEQ ID NO: 15)

These two DNA oligonucleotides were mixed together, each at an amount of 0.1 µg, denatured at 100° C. for 5 minutes, and then annealed by slow cooling. The resulting liker was phosphorylated with T4 bacteriophage polynucleotide kinase after annealing. The phosphorylated linker was ligated into pUC19 between the EcoR I and the Hind III sites. The resulting plasmid was called pCLON3 (for the cloning method, see also "Guidelines of Clone Experiments", Science Publishing House, 1992). pCLON3 contains multiple cloning sites for the following enzymes: Age I and Hind III.

The insulator of the chicken β-globin gene locus is a DNA fragment of about 1,200 bp, located within a 5' boundary element of the chicken β-globin locus. Further researches indicated that near half of the insulator activity of said fragment was due to a CpG island-like structure (i.e., so-called "core element") having a length of about 250 bp and containing a DNase I hypersensitive site (5'HS4) located 5' of the fragment. The chicken globin insulator contains bp 1-239 of the cDNA sequence of Gallus gallus beta-globin insulator in Gen Bank (Ben Bank number accession U78775, see The full sequence of the segment containing the mouse cytomegalovirus promoter of pDC315, multiple cloning sites and SV40 poly A signal as well as two flanking insulators was synthesized by Shanghai Justbest Gene Technology Company, and the sequence was as follows:

(SEQ ID NO: 16)
Actagt (Spe I)GAGCTCACGGGACAGCCCCCCCCAAAGCCCCCAG

GGATGTAATTACGTCCCTCCCCCGCTAGGGGGCAGCAGCGAGCCGCCCGG

GGCTCCGCTCCGGTCCGGCGCTCCCCCCGCATCCCCGAGCCGGCAGCGTG

CGGGGACAGCCCGGGCACGGGGAAGGTGGCACGGGATCGCTTTCCTCTGA

ACGCTTCTCGCTGCTCTTTGAGCCTGCAGACACCTGGGGGATACGGGGAA

AAtctagtGAGCTCACGGGACAGCCCCCCCCAAAGCCCCCAGGGATGT

AATTACGTCCCTCCCCCGCTAGGGGGCAGCAGCGAGCCGCCCGGGGCTCC

GCTCCGGTCCGGCGCTCCCCCCGCATCCCCGAGCCGGCAGCGTGCGGGGA

CAGCCCGGGCACGGGGAAGGTGGCACGGGATCGCTTTCCTCTGAACGCTT

CTCGCTGCTCTTTGAGCCTGCAGACACCTGGGGGATACGGGGAAAA (Insulator x 2)

(murine CMV promoter)GATATACTGAGTCATTAGGGACTTTCCAA

TGGGTTTTGCCCAGTACATAAGGTCAATAGGGGTGAATCAACAGGAAAGT

CCCATTGGAGCCAAGTACACTGAGTCAATAGGGACTTTCCATTGGGTTTT

GCCCAGTACAAAAGGTCAATAGGGGGTGAGTCAATGGGTTTTTCCCATTA

TTGGCACGTACATAAGGTCAATAGGGGTGAGTCATTGGGTTTTTCCAGCC

ATTTAATTAAAACGCCATGTACTTTCCCACCATTGACGTCAATGGGCTAT

TGAAACTAATGCAACGTGACCTTTAAACGGTACTTTCCCATAGCTGATTA

ATGGGAAAGTACCGTTCTCGAGCCAATACACGTCAATGGGAAGTGAAAGG

GCAGCCAAAACGTAACACCGCCCCGGTTTTCCCCTGGAAATTCCATATTG

GCACTCATTCTATTGGCTGAGCTGCGTTCTACGTGGGTATAAGAGGCGCG

ACCAGCGTCGGTACCGTCGCAGTCTTCGGTCTGACCACCGTAGAACGCAG

ATC(murine CMV promoter)(multiple cloning site)GAA

TTCAAGCTGCTAGCAAGGATCCAGCTTGTCGACT(multiple cloning site)

(SV40 poly A)TCGAGCAACTTGTTTATTGCAGCTTATAATGGTTACA

AATAAAGCAATAGCATCACAAATTTCACAAATAAAGCATTTTTTTCACTG

CATTCTAGTTGTGGTTTGTCCAAACTCATCAATGTATCTTATCATGTCTG

GATCGTCTAGCATCGAAGATCC(SV40 poly A)

-continued

```
(Insulator X 2)GAGCTCACGGGGACAGCCCCCCCCAAAGCCCCA

GGGATGTAATTACGTCCCTCCCCCGCTAGGGGGCAGCAGCGAGCCGCCCG

GGGCTCCGCTCCGGTCCGGCGCTCCCCCCGCATCCCCGAGCCGGCAGCGT

GCGGGGACAGCCCGGGCACGGGGAAGGTGGCACGGGATCGCTTTCCTCTG

AACGCTTCTCGCTGCTCTTTGAGCCTGCAGACACCTGGGGGATACGGGGA

AAAtctagtGAGCTCACGGGGACAGCCCCCCCCAAAGCCCCAGGGATG

TAATTACGTCCCTCCCCCGCTAGGGGGCAGCAGCGAGCCGCCCGGGGCTC

CGCTCCGGTCCGGCGCTCCCCCCGCATCCCCGAGCCGGCAGCGTGCGGGG

ACAGCCCGGGCACGGGGAAGGTGGCACGGGATCGCTTTCCTCTGAACGCT

TCTCGCTGCTCTTTGAGCCTGCAGACACCTGGGGGATACGGGGAAAA tctaga(Xba I)
```

After being digested by Age I+Hind III, the segment was inserted into pClon3 between the Age I and the Hind III sites, resulting in a chicken globin insulator expression vector designated as pSGEI. It contains the multiple cloning sites for the following endonucleases in sequence: EcoR I, Nhe I, BamH I and Sal I.

pClone2-SG-HER was cleaved by EcoR I+Xho I, and was inserted into the chicken globin insulator expression vector pSGEI between the EcoR I and the Sal I sites to produce the resulting plasmid pSGEI-SG-HER. It was then digested by Xba I+Spe I to produce a fragment of 4925 bp, which was subsequently inserted into the Nhe I site of pDC311. The resulting plasmid was designated as pAdSGEI-SG-HER.

293 cell line was commercially available from Microbix Biosystem Inc. (Toronto, Canada), which was obtained by transforming human embryonic kidney cells with a cleaved type 5 adenovirus DNA. Said cell line comprises E1 region of type 5 adenovirus and expresses it, and can be transfected by adenovirus DNA at a high efficiency. When 293 cell line was co-transfected by a plasmid comprising the left arm of type 5 adenovirus and a plasmid comprising the right arm of type 5 adenovirus, infection-competent adenovirus can be produced through homologous recombination. pDC315-SG-EGFR and the plasmid pBHGlox(delta)E1Cre containing the right arm of type 5 adenovirus were co-transfected into 293 cell line via Lipofectamine transfection. pDC315-SG-HER, pDC315-SG-ECD20, pYQ10-SG-HER and pAdSGEI-SG-HER were separately co-transfected with the plasmid pBHGlox(delta)E1,3Cre containing the right arm of type 5 adenovirus into 293 cell line via Lipofectamine transfection. Recombinant virus plaques appeared 9-14 days after the co-transfection. The recombinant virus plaques were purified for three times, resulting in a proliferation-deficient adenovirus Ad-SG-EGFR carrying the gene encoding human antibody SG-EGFR against human epidermal growth factor receptor 1 (EGFR), a proliferation deficient adenovirus Ad-SG-HER carrying the gene encoding the humanized antibody SG-HER against human epidermal growth factor receptor 2 (Her2), a proliferation deficient adenovirus Ad-SG-CD20 carrying the gene encoding the anti-human CD20 human-murine chimeric antibody SG-CD20, a proliferation-deficient adenovirus Adi-SG-HER carrying the gene encoding the humanized antibody SG-HER against human epidermal growth factor receptor 2 (Her2) and also comprising a hybrid intron inserted downstream of the MCMV promoter, a proliferation-deficient adenovirus AdEI-SG-HER carrying the gene encoding the humanized antibody SG-HER against human epidermal growth factor receptor 2 (Her2) and also comprising insulators both upstream and downstream of the expression cassette. The recombinant adenoviruses were called SG001, SG002, SG003, SG102 and SG202 respectively.

The recombinant adenovirus strains Ad-SG-HER and Adi-SG-HER have been deposited on Sep. 21, 2012 as CCTCC No. V201241 and CCTCC No. V201243, respectively, in the public depository identified as China Center for Type Culture Collection (CCTCC), Wuhan University, Bayi Road 299, Wuchang District, Wuhan City, Hubei Province, China, Post code: 430072.

The recombinant viruses constructed above were listed in the following table:

| Recombinant virus | Name | Plasmid containing Ad5 left arm | Plasmid containing Ad5 right arm |
|---|---|---|---|
| Ad-SG-EGFR | SG001 | pDC315-SG-EGFR | pBHGlox(delta)E1Cre |
| Ad-SG-HER | SG002 | pDC315-SG-HER | pBHGlox(delta)E1,3Cre |
| Ad-SG-CD20 | SG003 | pDC315-SG-CD20 | pBHGlox(delta)E1,3Cre |
| Adi-SG-HER | SG102 | pYQ10-SG-HER | pBHGlox(delta)E1,3Cre |
| AdEI-SG-HER | SG202 | pAdSGEI-SG-HER | pBHGlox(delta)E1,3Cre |

The recombinant viruses were abundantly propagated in 293 cells, and purified by cesium chloride gradient centrifugation in a large scale (see also, Gene Transfer and Expression Protocols, Edited by Murray E J, Humana Press 1991, "Document 2"). Ad-SG-EGFR (SG001) was a type 5 adenovirus with the deletion of E1 region (deletion of bp342-bp3523 of the adenovirus) and the insertion of murine cytomegalovirus (MCMV) IE promoter, the light chain gene and the heavy chain gene encoding the human antibody SG-EGFR against human epidermal growth factor receptor 1, the polycistron of encephalomyocarditis virus and the SV40 poly A signal sequence. The other DNA sequences of the recombinant adenovirus were identical to those of the type 5 adenovirus. Ad-SG-HER (SG002) was a type 5 adenovirus with the deletion of E1 region (deletion of bp342-bp3523 of adenovirus) and the insertion of murine cytomegalovirus (MCMV) IE promoter, the light chain gene and the heavy chain gene encoding the human antibody SG-HER against human epidermal growth factor receptor 2, the polycistron of encephalomyocarditis virus and the SV40 poly A signal sequence. Moreover, the plasmid Ad-SG-HER further contained a deletion of bp28133-bp30818 (partial sequence of E3 region). The other DNA sequences of the recombinant adenovirus were identical to those of the type 5 adenovirus. Ad-SG-CD20 (SG003) was a type 5 adenovirus with the deletion of E1 region (deletion of bp342-bp3523 of adenovirus) and the insertion of murine cytomegalovirus (MCMV) IE promoter, the light chain gene and the heavy chain gene encoding the human antibody SG-CD20 against human epidermal growth factor receptor 1, the polycistron of encephalomyocarditis virus and the SV40 poly A signal sequence. Moreover, Ad-SG-CD20 further contained a deletion of bp28133-bp30818 (partial sequence of E3 region). The other DNA sequences of the recombinant adenovirus were identical to those of the type 5 adenovirus. Adi-SG-HER (SG102) was a type 5 adenovirus with the deletion of E1 region (deletion of bp342-bp3523 of adenovirus), the insertion of murine cytomegalovirus (MCMV) IE promoter and the hybrid intron comprising the 5' splicing site of the third leader sequence of adenovirus major later mRNA and the 3' splicing site of immunoglobin, the light chain gene and the heavy chain gene encoding the human antibody SG-HER against human epidermal growth factor receptor 2, the polycistron of encephalomyocarditis virus and the SV40 poly A signal sequence. Moreover, Adi- SG-HER further contained a deletion of bp28133-bp30818 (partial sequence of E3 region). The other DNA sequences of the recombinant adenovirus were identical to those of the type 5 adenovirus. AdEI-SG-HER (SG202) was a type 5 adenovirus with the deletion of E1 region (deletion of bp342-bp3523 of adenovirus) and the insertion of murine cytomegalovirus (MCMV) IE promoter, the light chain gene and the heavy chain gene encoding the human antibody SG-HER against human epidermal growth factor receptor 2, the polycistron of encephalomyocarditis virus and the SV40 poly A signal sequence. It further contained two chicken globin insulators located separately upstream and downstream of the expression cassette. Moreover, AdEI-SG-HER further contained a deletion of bp28133-bp30818 (partial sequence of E3 region). The other DNA sequences of the recombinant adenovirus were identical to those of the type 5 adenovirus.

Example 3

Recombination of the Proliferation Deficient Adeno-Associated Virus Carrying a Gene Encoding a Humanized Antibody SG-HER Against Human Epidermal Growth Factor Receptor 2 (her2)

The type 2 adeno-associated viral vector pTR was a gift from Dr. Shi Wenfang of Ohio Medical College (US), and the pSH3 vector was a gift from Prof. James P. Trempe of Biochemical and Molecular Biology Department of Ohio Medical College (US). The vector pTR comprised two terminal repeat sequences ITR and the packaging signal sequence Ψ of the type 2 adeno-associated virus, and pSH3 comprised E4, E2a and VA of the type 5 adenovirus as well as cap and rep of the type 2 adeno-associated virus.

The pClone2-SG-HER was digested by EcoR I+Xho I, and directly inserted into the pTR vector between the EcoR I and the Sal I sites to generate a plasmid named pTR-SG-HER.

The pTR-SG-HER and pSH3 were co-transfected into 293 cell line via Lipofectamine. 72 hours after co-transfection, the cells and the supernatant were collected, and the recombinant adeno-associated virus was purified by cesium chloride gradient centrifugation (for the method, see also the Document 2). Thus, the proliferation deficient adeno-associated virus AAV-SG-HER carrying a gene encoding the humanized antibody SG-HER against human epidermal growth factor receptor 2 (Her2) was obtained.

Example 4

In Vitro Expression of the Humanized Antibody by the Recombinant Adenvirus (SG002) Carrying a Gene Encoding the Humanized Antibody SG-HER Against Human Epidermal Growth Factor Receptor 2 (her2)

One normal cell line, namely the lung fibroblast cell line WI-38, another normal cell line, namely the lung fibroblast cell line B J, and a tumor cell line SK-Br-3 which was positive to human epidermal growth factor 2 (Her2) were commercially available from ATCC Company (US). These cell lines were plated on 6-well plates at a density of $5 \times 10^5$ cells per well, and cultured at 37° C. and 5% $CO_2$ in an incubator. 1 ml of serum-free medium was replaced on the second day, and then the control adenovirus Ad5-Lac Z, or the recombinant adenovirus SG002 carrying a gene encoding the humanized antibody SG-HER against human epidermal growth factor receptor 2 (Her2), or the proliferation deficient adenovirus SG102 carrying a gene encoding the humanized antibody SG-HER against human epidermal growth factor receptor 2 (Her2) and further containing a hybrid intron inserted downstream of the MCMV promoter were added respectively at an amount of $5 \times 10^6$/well. After being cultured for 90 minutes, the cells were washed with phosphate buffer (PBS) twice to remove the viruses, and then cultured in 3 ml of culture medium supplemented with 5% fetal bovine serum. Supernatants were separately collected after 72 hr. The expression levels in the supernatants were quantitatively detected by sandwich enzyme-linked immunosorbent assay (ELISA). The results showed that WI-38, BJ and SK-Br-2 all secreted large quantities of the humanized antibodies after they were infected with the recombinant adenoviruses SG002 and SG102 in vitro, wherein the expression levels of SG102 were obviously higher than those of SG002. However, the control adenovirus Ad5-Lac Z was negative in expression. The results were shown in FIG. 1.

Figure 2:
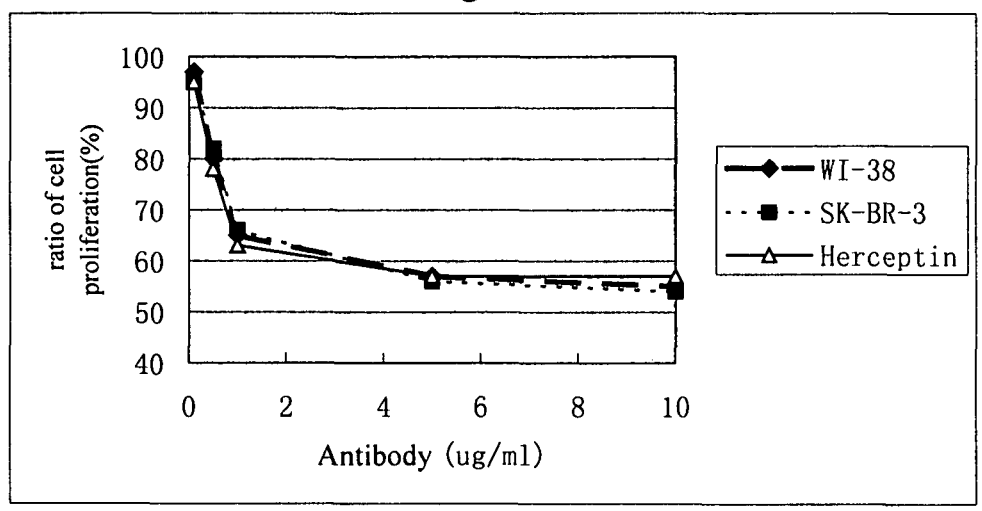
FIG. 2: the inhibitory effects of the humanized antibodies secreted in the supernatants of WI-38 and SK-Br-3 cells that are infected with the recombinant virus SG002, and Herceptin on the proliferation of the breast cancer cell SK-Br-3 that is positive to human epidermal growth factor receptor 2 (Her2) The rate of cell proliferation is expressed as the number of the treated cells/the number of the control cells×100%.

When the humanized antibodies secreted by the WI38 and SK-Br-3 that were infected by SG002 in vitro and Herceptin of Genentech Company (US) were separately added to a breast cancer cell line SK-Br-3 positive to human epithelial growth factor receptor 2 (Her 2) in an amount of 10 µg/ml, 5 µg/ml, 1 µg/ml, 0.5 µg/ml, 0.1 µg/ml and 0 µg/ml, they exhibited similar cytotoxic effects to the cells (see also FIG. 2), which indicated that the humanized antibodies secreted by WI38 and SK-Br-3 transfected by SG002 in vitro brought about the same effects as Herceptin of Genentech Company (US).

Example 5

Therapeutic Effects of the Recombinant Adenovirus SG002 Carrying a Gene Encoding the Humanized Antibody SG-HER Against Human Epidermal Growth Factor Receptor 2 (her2) on the Treatment of Breast Tumors Transplanted into Nude Mice The effects of using the recombinant adenovirus SG002 carrying a gene encoding the humanized antibody SG-HER against human epidermal growth factor receptor 2 (Her2) for treating tumor xenografts positive to human epidermal growth factor receptor 2 (Her2) in nude mice were studied.

Breast cancer cell line BT-474 was commercially available from ATCC Company (US). Nude mice of 4-5 weeks were sc. inoculated with $1 \times 10^7$ of the breast cancer cell line BT-474 cells, and 100 $mm^3$ tumors were formed after 8 weeks. The mice were divided into untreated group, adenovirus control group (Ad-Lac Z) and treated group (SG002). The untreated group was subject to no therapy, and the adenovirus control group and the treated group were separately administered via mouse caudal vein with $1 \times 10^9$ pfu of the control adenovirus Ad5-Lac Z or the therapeutic recombinant virus SG002. The results showed that the volumes of the tumors in the untreated group and the control group increased 3 folds after 4 weeks, while the volume of the tumors in the treatment group was not significantly increased, with some tumors completely disappearing.

Example 6

Therapeutic Effects of the Recombinant Adenovirus SG002 Carrying a Gene Encoding the Humanized Antibody SG-HER Against Human Epidermal Growth Factor Receptor 2 (her2) on the Treatment of Ovarian Cancer Xenografts into Nude Mice The effects of using the recombinant adenovirus SG002 carrying a gene encoding the humanized antibody SG-HER against human epidermal growth factor receptor 2 (Her2) for treating tumor xenografts positive to human epidermal growth factor receptor 2 (Her2) in nude mice were studied.

Figure 3:
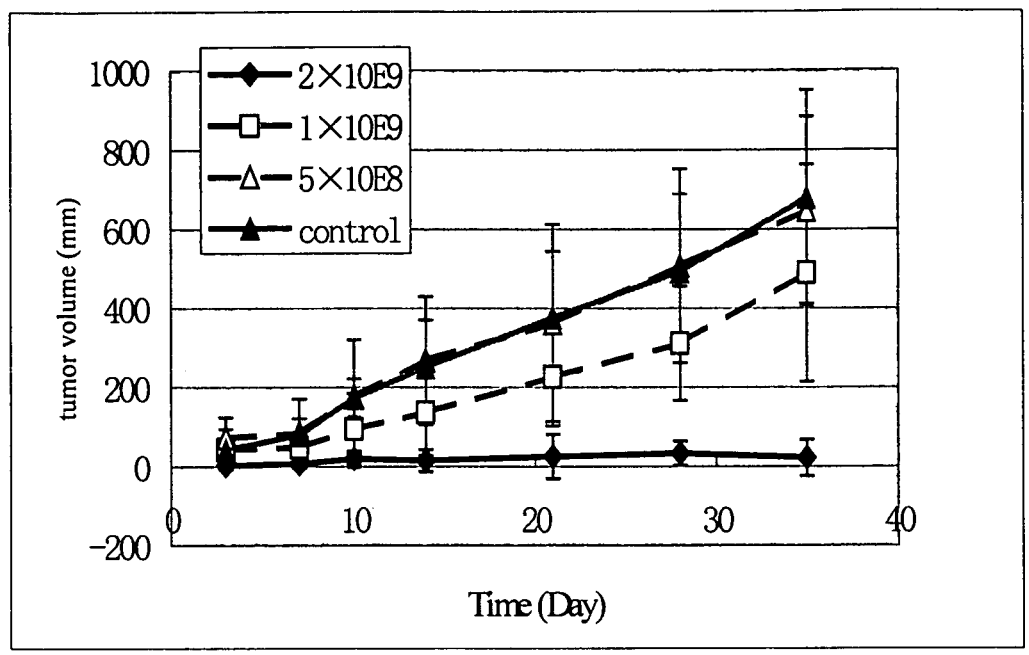
FIG. 3: the sizes of the tumors in Balb/c nude mice with human ovarian cancer cell line SK-OV-3 highly expressing HER2, wherein the mice are separately administered with recombinant adenovirus SG002 via tail vein at a dosage of $5×10^8$, $1×10^9$ or $5×10^9$ pfu respectively.
Figure 4:
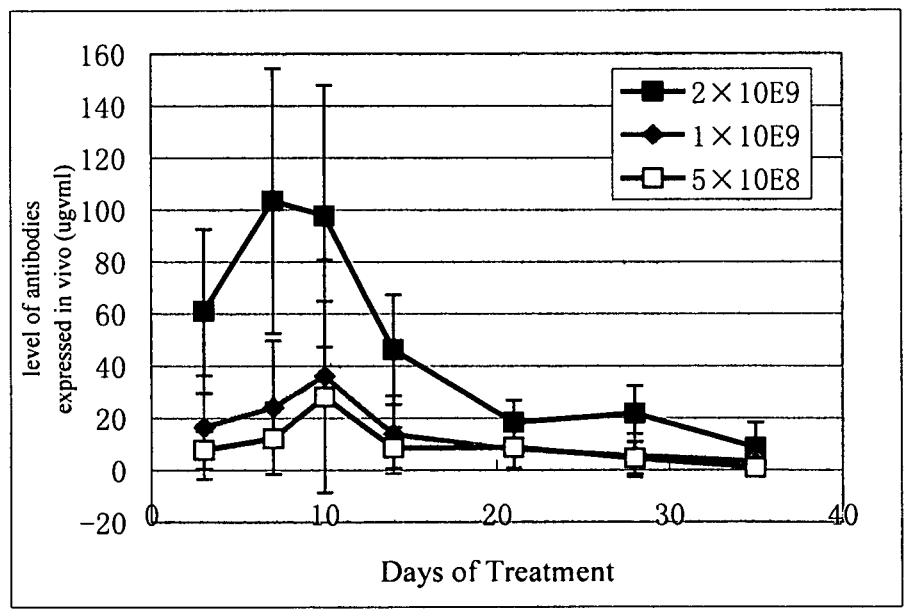
FIG. 4: the expression levels of the humanized antibodies in blood sera of the Balb/c nude mice with human ovarian cancer cell line SK-OV-3 highly expressing HER2, wherein the mice are respectively administered with recombinant adenovirus SG002 via tail vein at a dosage of $5×10^8$, $1×10^9$ or $5×10^9$ pfu respectively.

Ovarian cancer cell line SK-OV-3 was commercially available from ATCC Company (US). Nude mice of 4-5 weeks were sc. inoculated with $1\times10^7$ of the ovarian cancer cell line SK-OV-3 cells, and were divided into untreatment group, adenovirus control group (Ad-Lac Z), and low-dosage, medium-dosage and high-dosage treatment groups (SG002) after one week. The untreatment group was subject to no therapy; the adenovirus control group was administered via caudal vein with $2\times10^9$ pfu of the control adenovirus Ad5-Lac Z; and the low-dosage, medium-dosage and high-dosage treatment groups were administered via caudal vein with $5\times10^8$, $1\times10^9$, and $2\times10^9$ pfu of the therapeutic recombinant virus SG002. The tumor volumes were respectively measured on day 3, 7, 10, 14, 21, 28 and 35 post-treatment. The results were shown in FIG. 3. It can be seen that, with the increase of the therapeutic dosage, SG002 exhibited more significant therapeutic effect on ovarian cancer. The expression levels of the antibodies in mouse blood sera were quantitatively determined by sandwich enzyme-linked immunosorbent assay (ELISA), and the results were shown in FIG. 4. It can be seen that the expression levels of the antibodies increased with the increase of the therapeutic dosage, and could reached up to a level of 50-150 µg/ml.

What is claimed is:

1. A type 5 recombinant adenovirus, which is Ad-SG-HER or Adi-SG-H ER.

2. A method for expressing full-length antibody with human constant regions by the type 5 recombinant adenovirus according to claim 1, comprising infecting tumor cells in vitro with said type 5 recombinant adenovirus.

3. A method for expressing full-length antibody with human constant regions by the type 5 recombinant adenovirus according to claim 1, comprising infecting normal cells in vitro with said type 5 recombinant adenovirus.

4. A method for treating tumors of a mammal with the type 5 recombinant adenovirus according to claim 1 comprising the following steps:
   1) infecting tumor cells with said type 5 recombinant adenovirus in vivo or in vitro; and
   2) expressing the full-length antibody with human constant regions encoded by said type 5 recombinant adenovirus in tumor cells to inhibit the formation, growth and metastasis of tumors.

5. A method according to claim 4, further comprising administering a chemical antineoplastic agent before, when or after the tumor cells are infected with the recombinant virus.

6. A method for treating tumors of a mammal with the type 5 recombinant adenovirus according to claim 1 comprising the following steps:
   1) infecting normal cells with said type 5 recombinant adenovirus in vivo or in vitro; and
   2) expressing the tumor-therapeutic full-length antibody with human constant regions encoded by said type 5 recombinant adenovirus in normal cells to inhibit the formation, growth and metastasis of tumors.

7. A method according to claim 6, further comprising administering chemical anti-neoplastic agent before, when or after the normal cells are infected with the recombinant virus.

8. A pharmaceutical composition comprising the type 5 recombinant adenovirus according to claim 1 and a pharmaceutically acceptable carrier.

* * * * *

```
                          SEQUENCE LISTING

<160> NUMBER OF SEQ ID NOS: 18

<210> SEQ ID NO 1
<211> LENGTH: 36
<212> TYPE: DNA
<213> ORGANISM: artificial
<220> FEATURE:
<223> OTHER INFORMATION: primer

<400> SEQUENCE: 1
ggggtaccta gatcttagta atcaattacg gggtca                             36

<210> SEQ ID NO 2
<211> LENGTH: 42
<212> TYPE: DNA
<213> ORGANISM: artificial
<220> FEATURE:
<223> OTHER INFORMATION: primer

<400> SEQUENCE: 2
gagaagcttg tcgacgaatt cctagcggat ctgacggttc ac                      42

<210> SEQ ID NO 3
<211> LENGTH: 49
<212> TYPE: DNA
<213> ORGANISM: artificial
<220> FEATURE:
<223> OTHER INFORMATION: primer

<400> SEQUENCE: 3
gaattcgtcg acaagcttct cgagggatcc atctagataa ctgatcata              49

<210> SEQ ID NO 4
<211> LENGTH: 44
<212> TYPE: DNA
<213> ORGANISM: artificial
<220> FEATURE:
<223> OTHER INFORMATION: primer

<400> SEQUENCE: 4
atagtttagc ggccgctaag atctaagata cattgatgag tttg                    44

<210> SEQ ID NO 5
<211> LENGTH: 48
<212> TYPE: DNA
<213> ORGANISM: artificial
<220> FEATURE:
<223> OTHER INFORMATION: primer

<400> SEQUENCE: 5
ccggaattca tcgattctgt cgacctgcag gaattgcccc tctccctc                48
```

<210> SEQ ID NO 6
<211> LENGTH: 49
<212> TYPE: DNA
<213> ORGANISM: artificial
<220> FEATURE:
<223> OTHER INFORMATION: primer

<400> SEQUENCE: 6

| | |
|---|---|
| tgctctagac ccgggctcga gggatcctta atcatcgtgt ttttcaaag | 49 |

<210> SEQ ID NO 7
<211> LENGTH: 1368
<212> TYPE: DNA
<213> ORGANISM: artificial
<220> FEATURE:
<223> OTHER INFORMATION: Heavy chain of SG-EGFR

<400> SEQUENCE: 7

| | |
|---|---|
| cgcggatcca ccatggagtt ttggctgagc tgggttttcc ttgttgctat tttaaaaggt | 60 |
| gtccagtgtg tctctggtgg ctccgtcagc agtggtgatt actactggac ctggattcgg | 120 |
| cagtccccag ggaagggact ggagtggatt ggacacatct attacagtgg gaacaccaat | 180 |
| tataacccct ccctcaagag tcgactcacc atatcaattg acacgtccaa gactcagttc | 240 |
| tccctgaagc tgagttctgt gaccgctgcg gacacggcca tttattactg tgtgcgagat | 300 |
| cgagtgactg tgcttttga tatctggggc caagggacaa tggtcaccgt ctcttcagcc | 360 |
| tccaccaagg gcccatcggt cttccccctg gcaccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagaaagt tgagcccaaa | 660 |
| tcttgtgaca aaactcacac atgcccaccg tgcccagcac ctgaactcct ggggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatag taatctagaa agcttggg | 1368 |

<210> SEQ ID NO 8
<211> LENGTH: 665
<212> TYPE: DNA
<213> ORGANISM: artificial
<220> FEATURE:
<223> OTHER INFORMATION: Light chain of SG-EGFR

<400> SEQUENCE: 8

| | |
|---|---|
| ccggaattca ccatggaagc cccagctcag cttctcttcc tcctgctact ctggctccca | 60 |

```
gataccaccg gaaccatcac ttgccaggcg agtcaggaca tcagcaacta tttaaattgg    120
tatcagcaga aaccagggaa agcccctaaa ctcctgatct acgatgcatc caatttggaa    180 acagggtcc catcaaggtt cagtggaagt ggatctggga cagattttac tttcaccatc     240
agcagcctgc agcctgaaga tattgcaaca tatttctgtc aacactttga tcatctcccg    300
ctcgctttcg gcggagggac caaggtggag atcaaaactg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca caggggaga gtgtgataag     660 tcgac                                                                665

<210> SEQ ID NO 9
<211> LENGTH: 1599
<212> TYPE: DNA
<213> ORGANISM: artificial
<220> FEATURE:
<223> OTHER INFORMATION: Heavy chain of SG-HER

<400> SEQUENCE: 9
ggatccacca tgagcactga aagcatgatc cgggacgtgg agctggccga ggaggcgctc     60
cccaagaaga caggggggcc ccagggctcc aggcggtgct tgttcctcag cctcttctcc    120
ttcctgatcg tggcaggcgc caccacgctc ttctgcctgc tgcactttgg agtgatcggc    180
ccccagaggg aagagttccc cagggacctc tctctaatca gccctctggc ccaggcagag    240
gttcagctgg tggagtctgg cggtggcctg gtgcagccag ggggctcact ccgtttgtcc    300
tgtgcagctt ctggcttcaa cattaaagac acctatatac actgggtgcg tcaggccccg    360
ggtaagggcc tggaatgggt tgcaaggatt tatcctacga atggttatac tagatatgcc    420
gatagcgtca agggccgttt cactataagc gcagacacat ccaaaaacac agcctacctg    480
cagatgaaca gcctgcgtgc tgaggacact gccgtctatt attgttctag atggggaggg    540
gacggcttct atgctatgga ctactggggt caaggaaccc tggtcaccgt ctcctcggcc    600
tccaccaagg gcccatcggt cttccccctg gcaccctcct ccaagagcac ctctgggggc    660
acagcggccc tgggctgcct ggtcaaggac tacttccccg aaccggtgac ggtgtcgtgg    720
aactcaggcg ccctgaccag cggcgtgcac accttcccgg ctgtcctaca gtcctcagga    780
ctctactccc tcagcagcgt ggtgaccgtg ccctccagca gcttgggcac ccagacctac    840
atctgcaacg tgaatcacaa gcccagcaac accaaggtgg acaagaaagt tgagcccaaa    900
tcttgtgaca aaactcacac atgcccaccg tgcccagcac ctgaactcct ggggggaccg    960
tcagtcttcc tcttcccccc aaaacccaag gacaccctca tgatctcccg gacccctgag    1020
gtcacatgcg tggtggtgga cgtgagccac gaagaccctg aggtcaagtt caactggtac    1080
gtggacggcg tggaggtgca taatgccaag acaaagccgc gggaggagca gtacaacagc    1140
acgtaccgtg tggtcagcgt cctcaccgtc ctgcaccagg actggctgaa tggcaaggag    1200
tacaagtgca aggtctccaa caaagccctc ccagccccca tcgagaaaac catctccaaa    1260
gccaaagggc agccccgaga accacaggtg tacaccctgc ccccatcccg ggatgagctg    1320
accaagaacc aggtcagcct gacctgcctg gtcaaaggct tctatcccag cgacatcgcc    1380
```

-continued

| | |
|---|---|
| gtggagtggg agagcaatgg gcagccggag aacaactaca agaccacgcc tcccgtgctg | 1440 |
| gactccgacg gctccttctt cctctacagc aagctcaccg tggacaagag caggtggcag | 1500 |
| caggggaacg tcttctcatg ctccgtgatg catgaggctc tgcacaacca ctacacgcag | 1560 |
| aagagcctct ccctgtctcc gggtaaatag taactcgag | 1599 |

<210> SEQ ID NO 10
<211> LENGTH: 723
<212> TYPE: DNA
<213> ORGANISM: artificial
<220> FEATURE:
<223> OTHER INFORMATION: Light chain of SG-HER

<400> SEQUENCE: 10

| | |
|---|---|
| ccggaattca ccatggaagc cccagctcag cttctcttcc tcctgctact ctggctccca | 60 |
| gataccaccg gagatatcca gatgacccag tccccgagct ccctgtccgc ctctgtgggc | 120 |
| gatagggtca ccatcacctg ccgtgccagt caggatgtga atactgctgt agcctggtat | 180 |
| caacagaaac caggaaaagc tccgaaacta ctgatttact cggcatcctt cctctactct | 240 |
| ggagtccctt ctcgcttctc tggatccaga tctgggacgg atttcactct gaccatcagc | 300 |
| agtctgcagc cggaagactt cgcaacttat tactgtcagc aacattatac tactcctccc | 360 |
| acgttcggac agggtaccaa ggtggagatc aaaactgtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccaga gagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg ttgataagtc | 720 |
| gac | 723 |

<210> SEQ ID NO 11
<211> LENGTH: 1434
<212> TYPE: DNA
<213> ORGANISM: artificial
<220> FEATURE:
<223> OTHER INFORMATION: Heavy chain of SG-CD20

<400> SEQUENCE: 11

| | |
|---|---|
| cgcggatcca ccatggagtt ttggctgagc tgggttttcc ttgttgctat tttaaaaggt | 60 |
| gtccagtgtc aggtacaact gcagcagcct ggggctgagc tggtgaagcc tggggcctca | 120 |
| gtgaagatgt cctgcaaggc ttctggctac acatttacca gttacaatat gcactgggta | 180 |
| aaacagacac ctggtcgggg cctggaatgg attggagcta tttatcccgg aaatggtgat | 240 |
| acttcctaca atcagaagtt caaggcaag gccacattga ctgcagacaa atcctccagc | 300 |
| acagcctaca tgcagctcag cagcctgaca tctgaggact ctgcggtcta ttactgtgca | 360 |
| agatcgactt actacggcgg tgactggtac ttcaatgtct ggggcgcagg gaccacggtc | 420 |
| accgtctctg cagcctccac caagggccca tcggtcttcc cctggcacc ctcctccaag | 480 |
| agcacctctg ggggcacagc ggccctgggc tgcctggtca aggactactt ccccgaaccg | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc agcagcttg | 660 |
| ggcacccaga cctacatctg caacgtgaat cacaagccca gcaacaccaa ggtggacaag | 720 |
| aaagttgagc ccaaatcttg tgacaaaact cacacatgcc caccgtgccc agcacctgaa | 780 |

| | |
|---|---|
| ctcctgggggg gaccgtcagt cttcctcttc cccccaaaac ccaaggacac cctcatgatc | 840 |
| tcccggaccc ctgaggtcac atgcgtggtg gtggacgtga gccacgaaga ccctgaggtc | 900 |
| aagttcaact ggtacgtgga cggcgtggag gtgcataatg ccaagacaaa gccgcgggag | 960 |
| gagcagtaca acagcacgta ccgtgtggtc agcgtcctca ccgtcctgca ccaggactgg | 1020 |
| ctgaatggca aggagtacaa gtgcaaggtc tccaacaaag ccctcccagc ccccatcgag | 1080 |
| aaaaccatct ccaaagccaa agggcagccc cgagaaccac aggtgtacac cctgccccca | 1140 |
| tcccgggatg agctgaccaa gaaccaggtc agcctgacct gcctggtcaa aggcttctat | 1200 |
| cccagcgaca tcgccgtgga gtgggagagc aatgggcagc cggagaacaa ctacaagacc | 1260 |
| acgcctcccg tgctggactc cgacggctcc ttcttcctct acagcaagct caccgtggac | 1320 |
| aagagcaggt ggcagcaggg gaacgtcttc tcatgctccg tgatgcatga ggctctgcac | 1380 |
| aaccactaca cgcagaagag cctctccctg tctccgggta aatagtaatc taga | 1434 |

<210> SEQ ID NO 12
<211> LENGTH: 723
<212> TYPE: DNA
<213> ORGANISM: artificial
<220> FEATURE:
<223> OTHER INFORMATION: light chain of SG-CD20

<400> SEQUENCE: 12

| | |
|---|---|
| ccggaattca ccatggaagc cccagctcag cttctcttcc tcctgctact ctggctccca | 60 |
| gataccaccg gacaaattgt tctctcccag tctccagcaa tcctgtctgc atctccaggg | 120 |
| gagaaggtca caatgacttg cagggccagc tcaagtgtaa gttacatcca ctggttccag | 180 |
| cagaagccag gatcctcccc caaaccctgg atttatgcca catccaacct ggcttctgga | 240 |
| gtccctgttc gcttcagtgg cagtgggtct gggacttctt actctctcac catcagcaga | 300 |
| gtggaggctg aagatgctgc cacttattac tgccagcagt ggactagtaa cccacccacg | 360 |
| ttcggagggg ggaccaagct ggaaatcaaa cgtactgtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccagg agagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg ttgataagtc | 720 |
| gac | 723 |

<210> SEQ ID NO 13
<211> LENGTH: 246
<212> TYPE: DNA
<213> ORGANISM: artificial
<220> FEATURE:
<223> OTHER INFORMATION: Hybrid intron

<400> SEQUENCE: 13

| | |
|---|---|
| actagttaac cagtcacagt cgcaaggtag gctgagcacc gtggcgggcg gcagcgggtg | 60 |
| gcggtcgggg ttgtttctgg cggaggtgct gctgatgatg taattaaagt aggcggtctt | 120 |
| gagacggcgg atggtcgagg tgaggtgtgg caggcttgag atcgatctgg ccatacactt | 180 |
| gagtgacaat gacatccact ttgcctttct ctccacaggt gtccactccc aggtccaacc | 240 |
| gaattc | 246 |

<210> SEQ ID NO 14
<211> LENGTH: 16
<212> TYPE: DNA
<213> ORGANISM: artificial
<220> FEATURE:
<223> OTHER INFORMATION: primer

<400> SEQUENCE: 14
aattgaccgg tagcta                                                   16

<210> SEQ ID NO 15
<211> LENGTH: 15
<212> TYPE: DNA
<213> ORGANISM: artificial
<220> FEATURE:
<223> OTHER INFORMATION: primer

<400> SEQUENCE: 15
gcttagctac cggtc                                                    15

<210> SEQ ID NO 16
<211> LENGTH: 1704
<212> TYPE: DNA
<213> ORGANISM: artificial
<220> FEATURE:
<223> OTHER INFORMATION: a synthetic segment containing mouse CMV
      promoter, multiple cloning site, and SV40 polyA signal
      as well as two flanking insulators

<400> SEQUENCE: 16
actagtgagc tcacggggac agccccccc caaagccccc agggatgtaa ttacgtccct      60
cccccgctag ggggcagcag cgagccgccc ggggctccgc tccggtccgg cgctcccccc    120 gcatcccga gccggcagcg tgcgggaca gcccgggcac ggggaaggtg gcacgggatc      180
gctttcctct gaacgcttct cgctgctctt tgagcctgca gacacctggg ggatacgggg    240
aaaatctagt gagctcacgg ggacagcccc ccccaaagc ccaggat gtaattacgt        300 ccctcccccg ctagggggca gcgagcc gcccggggct ccgctccggt ccggcgctcc      360
ccccgcatcc ccgagccggc agcgtgcggg gacagcccgg gcacggggaa ggtggcacgg    420
gatcgctttc ctctgaacgc ttctcgctgc tctttgagcc tgcagacacc tgggggatac    480
ggggaaaaga tactgagt cattagggac ttttccaatgg ttttgccca gtacataagg     540 tcaatagggg tgaatcaaca ggaaagtccc attggagcca agtacactga gtcaatagggg   600 actttccatt gggttttgcc cagtacaaaa ggtcaatagg gggtgagtca atgggttttt    660
cccattattg gcacgtacat aaggtcaata ggggtgagtc attgggtttt ccagccatt    720 taattaaaac gccatgtact ttcccaccat tgacgtcaat gggctattga actaatgca    780 acgtgacctt taaacggtac tttcccatag ctgattaatg ggaaagtacc gttctcgagc    840 caatacgt caatgggaag tgaaagggca gccaaaacgt aacaccgccc cggttttcc       900 ctggaaattc catattggca ctcattctat ggctgagct gcgttctacg tgggtataag     960
aggcgcgacc agcgtcggta ccgtcgcagt cttcggtctg accaccgtag aacgcagatc   1020
gaattcaagc tgctagcaag gatccagctt gtcgacttcg agcaacttgt ttattgcagc   1080
ttataatggt tacaaataaa gcaatagcat cacaaatttc acaaataaag cattttttc    1140 actgcattct agttgtggtt tgtccaaact catcaatgta tcttatcatg tctggatcgt    1200
ctagcatcga agatccgagc tcacggggac agccccccc caaagccccc agggatgtaa    1260
ttacgtccct cccccgctag ggggcagcag cgagccgccc ggggctccgc tccggtccgg   1320

```
cgctccccce gcatcccega geeggcageg tgegggaca geceggeac ggggaaggtg    1380 gcacgggatc gctttcctct gaacgcttct cgctgctctt tgagcctgca gacacctggg    1440
ggatacgggg aaaatctagt gagctcacgg ggacagcccc ccccaaagc ccccagggat    1500 gtaattacgt ccctcccccg ctaggggca gcagcgagcc gcccggggct ccgctccggt    1560
ccggcgctcc ccccgcatcc ccgagccggc agcgtgcggg gacagcccgg gcacggggaa    1620
ggtggcacgg gatcgctttc ctctgaacgc ttctcgctgc tctttgagcc tgcagacacc    1680
tgggggatac ggggaaaatc taga                                            1704

<210> SEQ ID NO 17
<211> LENGTH: 32
<212> TYPE: DNA
<213> ORGANISM: artificial
<220> FEATURE:
<223> OTHER INFORMATION: primer

<400> SEQUENCE: 17
aattactagt caggaattca agcttagatc tg                                    32

<210> SEQ ID NO 18
<211> LENGTH: 32
<212> TYPE: DNA
<213> ORGANISM: artificial
<220> FEATURE:
<223> OTHER INFORMATION: primer

<400> SEQUENCE: 18
ctagcagatc taagcttgaa ttcctgacta gt                                    32
```